(12) United States Patent
Liu et al.

(10) Patent No.: US 12,134,837 B2
(45) Date of Patent: Nov. 5, 2024

(54) FUSION IMAGING GENE AND LENTIVIRAL EXPRESSION PLASMID, LENTIVIRUS, CELL, PREPARATION METHODS AND APPLICATIONS THEREOF

(71) Applicants: ACADEMY OF MILITARY MEDICAL SCIENCES, ACADEMY OF MILITARY SCIENCES OF CHINESE PLA, Beijing (CN); BEIJING JIUYU ONCOLGY CO., LTD., Beijing (CN)

(72) Inventors: Zhiqiang Liu, Beijing (CN); Zengqiang Yuan, Beijing (CN); Cui Wang, Beijing (CN); Xiaowen Xing, Beijing (CN); Bingshui Xiu, Beijing (CN); Shihong Liu, Beijing (CN)

(73) Assignees: ACADEMY OF MILITARY MEDICAL SCIENCES, ACADEMY OF MILITARY SCIENCES OF CHINESE PLA, Beijing (CN); BEIJING JIUYU ONCOLGY CO., LTD., Beijing (CN)

( * ) Notice: Subject to any disclaimer, the term of this patent is extended or adjusted under 35 U.S.C. 154(b) by 0 days.

(21) Appl. No.: 18/430,589

(22) Filed: Feb. 1, 2024

(65) Prior Publication Data
US 2024/0167021 A1 May 23, 2024

Related U.S. Application Data

(63) Continuation of application No. PCT/CN2022/080421, filed on Mar. 11, 2022.

(30) Foreign Application Priority Data

Aug. 2, 2021 (CN) .......................... 202110882190.4

(51) Int. Cl.
C40B 40/08 (2006.01)
C12N 15/10 (2006.01)
(Continued)

(52) U.S. Cl.
CPC .......... C40B 40/08 (2013.01); C12N 15/1086 (2013.01); C12N 15/65 (2013.01);
(Continued)

(58) Field of Classification Search
None
See application file for complete search history.

(56) References Cited

U.S. PATENT DOCUMENTS 5,976,796 A 11/1999 Szalay et al.

FOREIGN PATENT DOCUMENTS

| CN | 111234028 A | 6/2020 |
|----|-------------|--------|
| CN | 113584062 A | 11/2021 |
| WO | 2018014005 A1 | 1/2018 |

OTHER PUBLICATIONS

Notification to Grant Patent Right for Invention from SIPO in 202110882190.4 dated Feb. 21, 2022.
(Continued)

*Primary Examiner* — Christian C Boesen
(74) *Attorney, Agent, or Firm* — Pilloff Passino & Cosenza, LLP Rachel Pilloff; Sean Passino

(57) ABSTRACT

A fusion imaging gene and lentiviral expression plasmid, lentivirus and cell, and preparation methods and applications thereof are provided. The fusion imaging gene includes bioluminescence imaging gene, fluorescent protein gene and calcium imaging gene. The three genes are linked by linkers. The fusion gene is inserted into a modified lentiviral expression plasmid to obtain lentivirus particles carrying the fusion imaging gene.

17 Claims, 36 Drawing Sheets

Specification includes a Sequence Listing.

(51) Int. Cl.
  *C12N 15/65* (2006.01)
  *C12N 15/86* (2006.01)
(52) U.S. Cl.
  CPC .... *C12N 15/86* (2013.01); *C12N 2740/15022* (2013.01); *C12N 2740/15043* (2013.01)

(56) References Cited

OTHER PUBLICATIONS

First Search Report from SIPO in 202110882190.4 dated Dec. 1, 2021.
Supplemental Search Report from SIPO in 202110882190.4 dated Feb. 14, 2022.
Yong Qian et al., "A bioluminescent Ca2+ indicator based on a topological variant of GCaMP6s," ChemBioChem, Feb. 2019, pp. 516-550, vol. 20, issue 4.
Liu Ze-Yue et al., "Calcium imaging of activity of mice neurons in nucleus accumbens using GCaMP6f," Basic & Clinical Medicine, Jun. 2016, vol. 36, No. 6.
Wu Hon-Gxia et al., "Construction and identification of recombinant pseudorabies virus expressing DsRed and NnaoLuc dual reporter genes," Aug. 2017.
Dong Fei-Fei et al., "GCaMPs: promising tools for in vivo calcium imaging," Academic Journal of Second Military Medical University, Jan. 2013, pp. 83-87, vol. 34, No. 1.
First Office action for China Application No. 202110882190.4, mailed Dec. 8, 2021.
International Search Report in PCT/CN2022/080421 dated Jun. 17, 2022.
Written Opinion of the International Searching Authority in PCT/CN2022/080421 dated Jun. 17, 2022.

FUSION IMAGING GENE AND LENTIVIRAL EXPRESSION PLASMID, LENTIVIRUS, CELL, PREPARATION METHODS AND APPLICATIONS THEREOF

CROSS-REFERENCE TO RELATED APPLICATIONS

This application is a continuation of PCT/CN2022/080421, filed on Mar. 11, 2022 and claims priority of Chinese Patent Application No. 202110882190.4, filed on Aug. 2, 2021 the entire contents of which are incorporated herein by reference.

INCORPORATION BY REFERENCE STATEMENT

This statement, made under Rules 77 (b) (5) (ii) and any other applicable rule incorporates into the present specification of an XML file for a "Sequence Listing XML" (see Rule 831 (a)), submitted via the USPTO patent electronic filing system or on one or more read-only optical discs (see Rule 1.52 (e) (8)), identifying the names of each file, the date of creation of each file, and the size of each file in bytes gas follows:

| 1. | File name: | Sequence_347-147-PPH_15039 |
|---|---|---|
| 2. | Creation date: | Jan. 30, 2024 |
| 3. | Byte size: | 30,191 bytes |

TECHNICAL FIELD

The disclosure relates to the field of biotechnology, and in particular to fusion imaging gene and lentiviral expression plasmid, lentivirus, cell, preparation methods and applications thereof.

BACKGROUND

Imaging tracing of cell fate has extensive and important applications in the field of biomedical research, such as evaluation of cell response to specific stimuli, evaluation after cell transplantation and so on. Taking cell transplantation as an example, cell fate tracing, including survival, distribution, differentiation and functional integration, is an important index to evaluate safety and effectiveness of the cell. In previous studies, due to the lack of cell lines marked by multi-modal imaging gene, it is impossible to trace the survival/distribution, differentiation/morphology and functional integration of cells after transplantation in the same cell. In order to achieve the above-mentioned different tracing purposes, researchers can only adopt a compromise method, evaluate the survival/distribution, differentiation/morphology and functional integration of seed cells marked by different imaging genes respectively, and comprehensively analyze the fate of cells by synthesizing the tracking data of different marked cells. In a typical report of the study on the integration of transplanted embryonic neurons in the neocortex of the brain in the Nature article in 2016 (Nature, 2016, 539:248-253), in order to evaluate the structural integration of embryonic neurons in the host, a researchers transplanted neurons marked by red fluorescent protein and detected their structural integration through histopathology. In order to evaluate the functional integration of embryonic neurons in the receptor, neurons marked by Gcamp6f are transplanted, and their functional integration is evaluated by calcium imaging. Finally, the transplantation results of two kinds of cells jointly show that the transplanted embryonic neurons may realize structural and functional integration in the recipient brain. However, the above methods not only increase the cost and workload of research, but also may affect the reliability of the results because the evaluation of structural and functional integration is carried out in independent animals (that is, asynchronous evaluation). For example, functional integration may not occur in structurally integrated cells, and the level of structural integration of cells with functional integration is unknown. Therefore, it is of great significance to synchronously trace different fates of cells.

Obtaining seed cells marked by multi-modal imaging gene is the key to solve the simultaneous evaluation of different fates of cells, which has important application value. Lentivirus is the most commonly used vector for stable gene transfection marking, but there are no reports of lentiviral particles carrying multi-modal imaging gene (quantitative imaging, morphological imaging and functional imaging) and their transfected marked cells. The main reasons are that there are many technical difficulties in achieving the above objectives, including: firstly, the length of multiple reporter genes is large, which is difficult for ordinary lentiviral vectors to accommodate and successfully transfect target cells. In particular, the use of multiple promoters to drive the expression of each reporter gene will further increase the length of foreign genes, making it more difficult to achieve effective packaging of lentivirus particles and successful transfection of target cells; secondly, linking multiple reporter genes to form a fusion multi-modal imaging gene, and using one promoter to drive expression may save the length occupied by the promoter, but improper fusion will lead to functional inactivation due to the spatial interaction between gene products. In addition, the fusion gene may be too long to obtain high-activity lentivirus. It is of great scientific significance and practical value to overcome the problems of inserting large fragments of genes into lentiviruses and maintaining the function of fusion genes, and to construct lentiviruses carrying multi-modal imaging gene for further stable gene marking of multi-modal imaging gene in different cells.

SUMMARY

The objective of the present disclosure is to provide a lentivirus carrying the fusion multi-modal imaging genes and its application. The lentivirus particles may be transfected to prepare cells stably marked by multi-modal imaging gene, such as human pluripotent stem cells (embryonic stem cell (ESC)/induced pluripotent stem cell (iPSC)), and further, quantitative imaging detection at single cell level, cell morphology detection at histological level and calcium activity function detection at subcellular level may be realized simultaneously for the marked cells themselves and the cells from which they are differentiated.

The above objective of the present disclosure is achieved by the following technical scheme.

The present disclosure relates to fusion imaging gene. The fusion imaging gene includes a bioluminescence imaging gene, a fluorescent protein gene and a calcium imaging gene, and the three genes are linked by linkers.

Preferably, the bioluminescence imaging gene is selected from a Nanoluc gene.

Optionally, the fluorescent protein gene is selected from a mRuby2 gene.

More optionally, the calcium imaging gene is selected from a Gcamp6f gene.

The present disclosure also relates to a lentiviral expression plasmid carrying the fusion imaging gene mentioned above. Optionally, a sequence of the lentiviral expression plasmid carrying fusion imaging gene is shown in SEQ ID NO.2.

The present disclosure also relates to a preparation method of lentiviral expression plasmid, at least including following steps:

S21, modifying the lentiviral expression plasmid, where the modifying preferably includes:

S211, removing an EF-1α promoter in a pLenti-EF1α-FH-CMV-CopGFP&Puro plasmid by double restriction endonuclease digestion with SphI and BamHI to obtain a skeleton plasmid: a nucleotide sequence of the pLenti-EF1α-FH-CMV-CopGFP&Puro plasmid is shown in SEQ ID NO.3:

S212, inserting a human ubiquitin promoter hUbc into the skeleton plasmid through enzyme link to obtain a pLenti-Ubc-FH-CMV-CopGFP&Puro intermediate plasmid:

S213, removing a sequence from a downstream of Ubc to a Puro gene site in the pLenti-Ubc-FH-CMV-CopGFP&Puro plasmid by PmeI and BamHI double digestion, namely a nucleotide sequence from 3826 to 6112 in the nucleotide sequence shown in the SEQ ID NO.3:

S22, inserting the fusion imaging gene mentioned above into a modified lentiviral expression plasmid to obtain the lentiviral expression plasmid carrying a fusion gene probe.

Optionally, the fusion imaging gene is inserted into the modified intermediate plasmid by using same restriction sites at both ends of the fusion imaging gene to obtain a pLenti-Ubc-Nanoluc-mRuby2-Gcamp6f plasmid, and the lentiviral expression plasmid is obtained through transformation, sequencing, and so on, and a nucleotide sequence of the lentiviral expression plasmid is shown in SEQ ID NO.2.

The present disclosure also relates to a lentivirus carrying the fusion imaging gene mentioned above.

The present disclosure also relates to a preparation method of the lentivirus mentioned above, at least including following steps:

co-transfecting 293T cells by the pLenti-Ubc-Nanoluc-mRuby2-Gcamp6f plasmid and lentivirus packaging plasmids PAX2 and pMD2G to obtain lentivirus particles carrying the fusion imaging gene.

Optionally, a mass ratio of the pLenti-Ubc-Nanoluc-mRuby2-Gcamp6f plasmid, the plasmid PAX2 and the plasmid pMD2G is 3-4:1.5-2.5:0.5-1.5, preferably, 3:2:1.

The present disclosure also relates to a cell marked by the fusion imaging gene mentioned above or infected by the lentivirus mentioned above. Optionally, the cell is selected from a human H1 embryonic stem cell and a human pluripotent stem cell.

The present disclosure also relates to applications of the cell mentioned above. The applications comprise an application in cell imaging detection: an application in cell fate tracking: or an application in preparing preparations or kits for the cell fate tracking or the cell imaging detection. Optionally, the cell imaging detection is to simultaneously detect cell number imaging, morphological imaging and calcium activity function.

The technical scheme of the disclosure at least includes following beneficial effects.

The lentivirus carrying fusion imaging gene provided by the disclosure may be used for stable multi-modal imaging gene marking of various cells, realizes multi-modal imaging detection of cell number, cell morphology and cell calcium functional activity, simultaneously tracks the different fates of cells, and provides a more powerful tool for cell fate evaluation.

DETAILED DESCRIPTION OF THE EMBODIMENTS

In order to explain the embodiment of the present disclosure or the technical scheme in the prior art more clearly, in the following description, different "one embodiment" or "an embodiment" do not necessarily refer to the same embodiment. Different embodiments may be replaced or combined, and for those skilled in the art, other embodiments may be obtained according to these embodiments without creative efforts.

One aspect of an embodiment of the present disclosure relate to fusion imaging gene. The fusion imaging gene includes a bioluminescence imaging gene, a fluorescent protein gene and a calcium imaging gene, and the three genes are linked by linkers.

In a specific embodiment, the bioluminescence imaging gene is selected from Nanoluc gene: the fluorescent protein gene is selected from mRuby2 gene: the calcium imaging gene is selected from Gcamp6f gene.

In a specific embodiment, the linkers are selected from a polypeptide chain. The polypeptide chain preferably contains 2-8 amino acids, and more preferably, the amino acids in the polypeptide chain are selected from two, three or four of S (serine), L (leucine), D (aspartic acid) and G (glycine) to constitute a flexible polypeptide chain:

further preferably, the polypeptide chain is selected from S-L-D-S(SEQ ID NO.8, named as Linker 1) or G-S-S-G (SEQ ID No.9, named as Linker 2).

In a specific embodiment, the Nanoluc gene and the mRuby2 gene are linked by S-L-D-S; mRuby2 gene and Gcamp6f gene are linked by G-S-S-G. According to the research of the embodiment of the disclosure, it is found that the three reporter genes are fused and expressed through S-L-D-S and G-S-S-G flexible polypeptide chains respectively, which ensures the correct folding and activity of each gene product.

Figure 1:
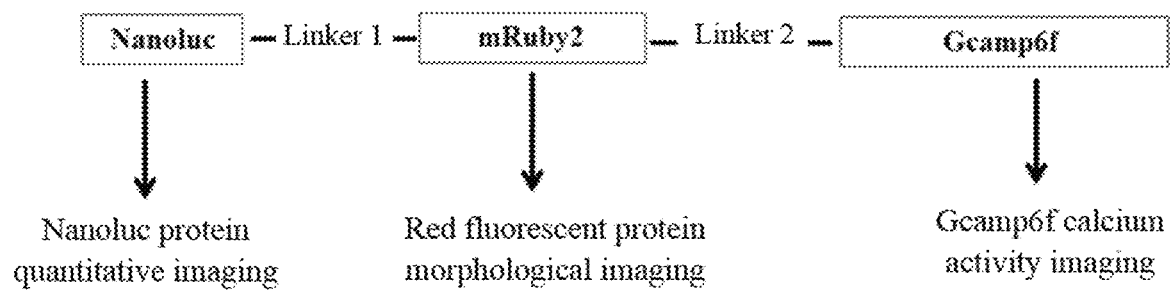
FIG. 1 is a schematic structural diagram of fusion multi-modal imaging genes in an embodiment of the present disclosure.

Specifically, the structural schematic diagram of the multi-modal imaging gene is shown in FIG. 1. The fused three reporter genes are Nanoluc for quantitative cellular imaging, mRuby2 for cellular morphological observation and Gcamp6f for cellular calcium activity functional imaging. Nanoluc and mRubi2 protein are linked by S-L-D-S (serine-leucine-aspartic acid-serine), and mRubi2 and Gcamp6f protein are linked by G-S-S-G (glycine-serine-serine-glycine), which may maintain the activity of each protein in the fused protein.

In a specific embodiment, a nucleotide sequence of the fusion imaging gene is shown in SEQ ID NO.1

Figure 17:
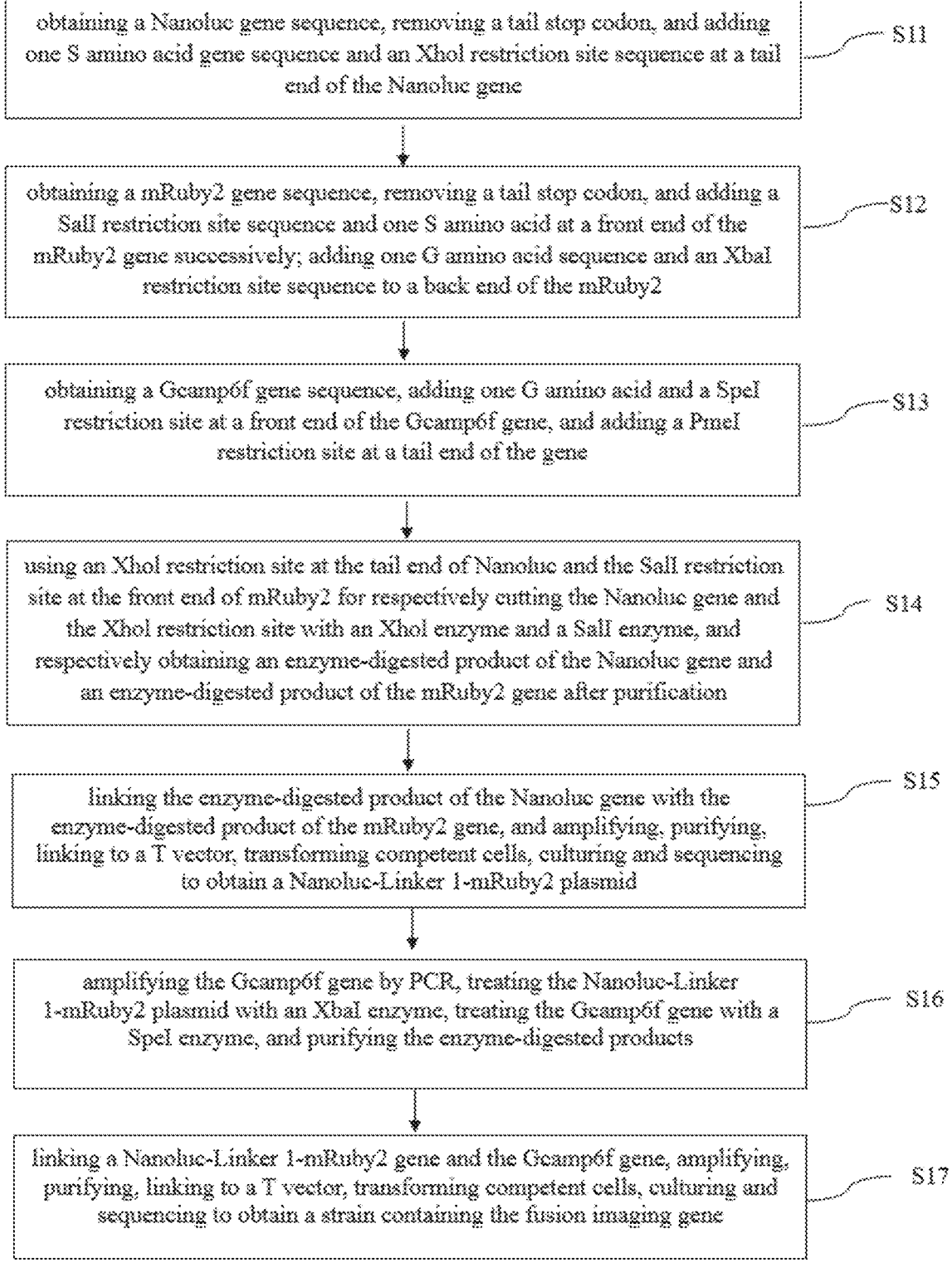
FIG. 17 is a process of method for constructing a fusion imaging gene.

Another aspect of an embodiment of the present disclosure also relates to a method for constructing the fusion imaging gene as shown in FIG. 17, at least including following steps:

S11, obtaining a Nanoluc gene sequence, removing a tail stop codon, and adding one S amino acid gene sequence and an XhoI restriction site sequence at a tail end of the Nanoluc gene, where the Nanoluc gene sequence is synthesized by the gene:

S12, obtaining a mRuby2 gene sequence, removing a tail stop codon, and adding a SalI restriction site sequence and one S amino acid at a front end of the mRuby2 gene successively; adding one G amino acid sequence and an XbaI restriction site sequence to a back end of the mRuby2, where the mRuby2 gene sequence is synthesized by the gene:

S13, obtaining a Gcamp6f gene sequence, adding one G amino acid and a SpeI restriction site at a front end of the Gcamp6f gene, and adding a PmeI restriction site at a tail end of the gene, where preferably the Gcamp6f gene sequence is obtained by Polymerase Chain Reaction (PCR) and more preferably, primer sequences are shown in SEQ ID NO.4 and SEQ ID NO.5;

S14, using the XhoI restriction site at the tail end of Nanoluc and the SalI restriction site at the front end of mRuby2 for respectively cutting the Nanoluc gene and the XhoI gene with an XhoI enzyme and a SalI enzyme, and respectively obtaining an enzyme-digested product of the Nanoluc gene and an enzyme-digested product of the mRuby2 gene after purification:

S15, linking an enzyme-digested product of the Nanoluc gene with an enzyme-digested product of the mRuby2 gene, and amplifying, purifying, linking to a T vector, transforming competent cells, culturing and sequencing to obtain a Nanoluc-Linker1-mRuby2 plasmid:

S16, amplifying the Gcamp6f gene by PCR, treating the Nanoluc-Linker1-mRuby2 plasmid with an XbaI enzyme, treating the Gcamp6f gene with a SpeI enzyme, and purifying the enzyme-digested products; and S17, linking a Nanoluc-Linker1-mRuby2 gene and the Gcamp6f gene, amplifying, purifying, linking to a T vector, transforming competent cells, culturing and sequencing to obtain a strain containing the fusion imaging gene.

Specific steps are as follows:

(1) Design and Construction of the Fusion Multi-Modal Imaging Gene 1) obtaining Nanoluc gene sequence by gene synthesis, removing the tail stop codon, and adding one S amino acid gene sequence (TCG) and XhoI restriction site sequence at the tail end of Nanoluc gene;

2) obtaining the gene sequence of red fluorescent protein mRuby2 by gene synthesis, removing the tail stop codon, and adding the SalI restriction site sequence (XhoI Isocaudamers) and one S amino acid (TCG) at the front end of mRuby2 successively, adding one G amino acid sequence (GGA) and XbaI restriction site sequence to the back end of mRuby2;

3) amplifying the Gcamp6f gene by PCR, where the plasmid carrying Gcamp6f gene comes from Beijing Maijin Biology Science and Technology Co., Ltd.; in the primer design, adding one G amino acid (GGA) and a SpeI restriction site (XbaI homotail enzyme) at the front end of the gene successively, and adding a PmeI restriction site at the end of the gene, where the primer sequence is as follows:

upstream primer (SEQ ID NO.4):
<u>actagt</u>ggaatgggttctcatcatcatcatcatggt (the underlined part is SpeI restriction site and G amino acid codon).

downstream primer (SEQ ID NO.5):
<u>gtttaaact</u>cacttcgctgtcatcatttgta (underlined part is PmeI restriction site);

4) using the XhoI restriction site at the tail end of Nanoluc and the SalI restriction site at the front end of mRuby2 for respectively cutting Nanoluc gene and XhoI gene with XhoI enzyme and SalI enzyme, and purifying the cut products by agarose electrophoresis;

5) utilizing the characteristics that XhoI and SalI are homotail enzymes, connecting the above-mentioned Nanoluc gene enzyme-digested product with the mRuby2 enzyme-digested product;

6) amplifying the ligation product by PCR, recycling and purifying the amplified product by agarose gel electrophoresis, and further linking the purified product to a T vector to transform DH5α competent cells;

7) coating the transformed cells on Luria-Bertani (LB) solid culture medium containing ampicillin and culturing in an incubator at 37° C. for 24 hours;

8) selecting bacterial monoclones, transferring them to test tubes (LB liquid medium containing ampicillin) for amplification and numbering, and culturing until the culture solution is turbid;

9) taking 1 mL of the bacterial liquid in each test tube and submitting it to a sequencing company for sequencing, so as to determine the Nanoluc-Linker1-mRruby2 plasmid with completely correct gene sequence and storing it for later use;

10) amplifying the Gcamp6f gene by PCR, treating the Nanoluc-Linker1-mRuby2 gene with XbaI enzyme, treating the Gcamp6f gene with SpeI enzyme, and purifying the enzyme-digested products by agarose gel electrophoresis; and 11) repeating the above steps of 5)-9), and obtaining the strain containing the fusion gene Nanoluc-Linker1-mRuby2-Linker2-Gcamp6f through ligation, transformation, sequencing, etc., and storing it for later use.

Another aspect of an embodiment of the present disclosure provides a lentiviral expression plasmid of the fusion imaging gene mentioned above. Preferably, a sequence of the lentiviral expression plasmid carrying fusion imaging gene is shown in SEQ ID NO.2.

Figure 2:
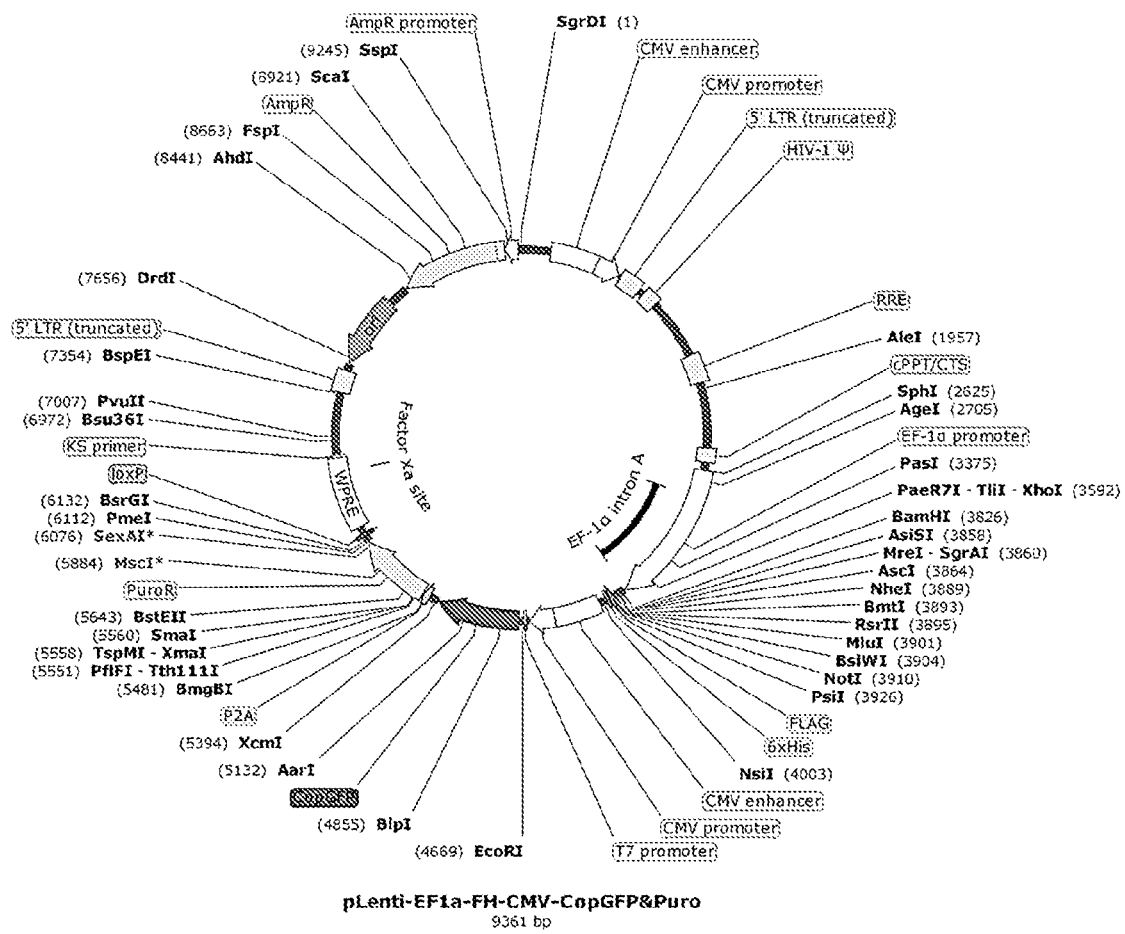
FIG. 2 is an original plasmid map of lentivirus used for modification in an embodiment of the present disclosure.

Another aspect of an embodiment of the present disclosure provides a preparation method of lentiviral expression plasmid of fusion imaging gene mentioned above. Because the total length of the fusion multi-modal imaging gene is large, inserting the conventional lentiviral expression plasmid may lead to low success rate of virus packaging and low activity, and it is difficult to carry out cell transfection in the later stage. Therefore, this disclosure takes pLenti-EF1α-FH-CMV-CopGFP&Puro plasmid from Weizhen Bioscience Incorporation as the skeleton (the original plasmid map of lentivirus used for modification is shown in FIG. 2, and the nucleotide sequence is shown in SEQID NO.3). Firstly, in order to ensure the gene to be widely expressed in different cells, the EF1α promoter is removed by enzyme digestion and replaced by the adult ubiquitination promoter hUbc. Subsequently, the sequence from the downstream of Ubc promoter to Puro gene is deleted by enzyme digestion, which provides more space for the insertion of foreign genes.

Figure 18:
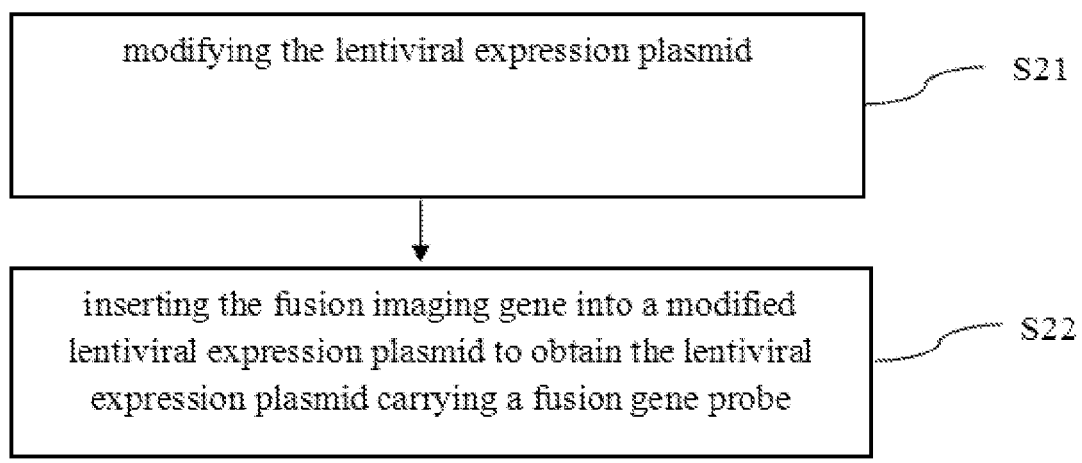
FIG. 18 is a process of a preparation method of lentiviral expression plasmid.

The preparation method of lentiviral expression plasmid at least includes following steps, as shown in FIG. 18:

S21, modifying the lentiviral expression plasmid: preferably including:

S211, removing an EF-1α promoter in a pLenti-EF1α-FH-CMV-CopGFP&Puro plasmid by double restriction endonuclease digestion with SphI and BamHI to obtain a skeleton plasmid:

S212, inserting a human ubiquitin promoter hUbc into the skeleton plasmid through enzyme link to obtain a pLenti-Ubc-FH-CMV-CopGFP&Puro intermediate plasmid; and S213, removing a sequence from a downstream of Ubc to a Puro gene site in the pLenti-Ubc-FH-CMV-CopGFP&Puro plasmid by PmeI and BamHI double digestion, namely a nucleotide sequence from 3826 to 6112 in the nucleotide sequence shown in the SEQ ID NO.3:

S22, inserting the fusion imaging gene mentioned above into a modified lentiviral expression plasmid to obtain the lentiviral expression plasmid carrying a fusion gene probe; preferably including:

inserting the fusion imaging gene into the modified intermediate plasmid by using same restriction sites at both ends of the fusion imaging gene to obtain a pLenti-Ubc-Nanoluc-mRuby2-Gcamp6f plasmid, and obtaining the lentiviral expression plasmid through transformation, sequencing, and so on.

Figure 3:
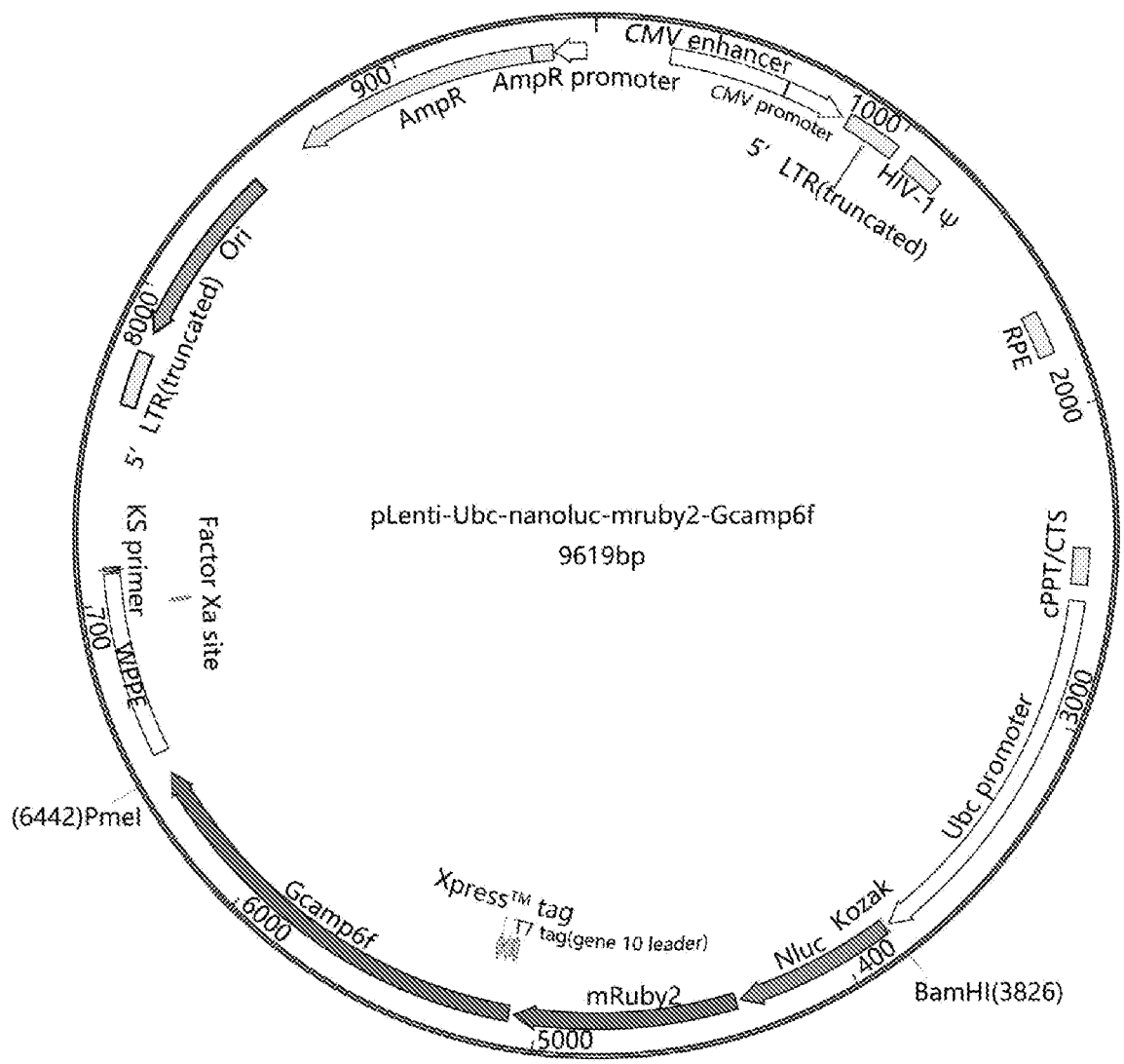
FIG. 3 is a lentiviral expression plasmid map carrying the fusion multi-modal imaging genes constructed in an embodiment of the present disclosure.

Specifically, the modification of lentiviral expression plasmid and the insertion of fusion imaging gene are mainly realized by the following steps:

1) removing an EF-1α promoter in a pLenti-EF1α-FH-CMV-CopGFP&Puro plasmid by double restriction endonuclease digestion with SphI and BamHI;
2) inserting a human ubiquitin promoter hUbc into the skeleton plasmid through enzyme link to replace the EF-1α promoter, obtaining a pLenti-Ubc-FH-CMV-CopGFP&Puro intermediate plasmid, and obtaining the plasmid with completely correct sequencing through transformation and sequencing;
3) removing a sequence from a downstream of Ubc to a Puro gene site in the pLenti-Ubc-FH-CMV-CopGFP&Puro plasmid by BamHI and PmeI double digestion, namely a nucleotide sequence from 3826 to 6112 in the nucleotide sequence shown in the SEQ ID NO.3;
4) using the prepared NanoLuc-mRuby2-Gcamp6f to fuse the same restriction sites (BamHI and PmeI) at both ends of the multiple reporter genes, and inserting the fusion gene into the restriction plasmid to obtain the pLenti-Ubc-NanoLuc-mRuby2-Gcamp6f plasmid, and obtaining the lentiviral expression plasmid with completely correct sequence through transformation, sequencing, etc. The lentiviral expression plasmid map of the obtained multi-modal imaging gene is shown in FIG. 3. The fusion multi-modal imaging gene is driven by UBC promoter, and the plasmid skeleton is modified to delete the screening genes such as puro and the promoter sequence in the original plasmid in FIG. 2, providing more space for the insertion of foreign genes. The total length of expression plasmid remains below 10000 bp after the insertion of fusion multi-modal imaging gene, which is equivalent to the length of conventional lentiviral expression plasmid.

Another aspect of the embodiment of the disclosure relate to a lentivirus carrying the fusion imaging gene. This lentivirus may be used for transfection marking of different cells to obtain cells stably marked by fusion imaging gene. The cells may be used for multi-modal imaging tracking of different fates of cells, including quantitative imaging, morphological imaging and calcium activity functional imaging.

Another aspect of the embodiment of the present disclosure relates to a preparation method of the lentivirus, and the lentivirus carrying the fusion imaging gene is obtained by co-transfecting cells by the pLenti-Ubc-Nanoluc-mRuby2-Gcamp6f plasmid and lentivirus packaging plasmids and packaging, at least including the following steps:

co-transfecting 293T cells by pLenti-Ubc-Nanoluc-mRuby2-Gcamp6f plasmid and lentivirus packaging plasmids PAX2 and pMD2G to obtain lentivirus particles carrying fusion imaging gene.

Preferably, the mass ratio of pLenti-Ubc-Nanoluc-mRuby2-Gcamp6f plasmid, plasmid PAX2 and plasmid pMD2G is 3:2:1.

Another aspect of the embodiment of the present disclosure relates to the cells marked by the fusion imaging gene or the cells infected by the lentivirus. Preferably, the cells are selected from human H1 embryonic stem cells and human pluripotent stem cells.

Another aspect of the embodiment of the disclosure relates to the applications of the cells in simultaneously realizing cell number imaging, morphological imaging and calcium activity function imaging detection.

Embodiment 1: Preparation of Lentivirus Particles Carrying Fusion Multi-Modal Imaging Gene (1) Design and Construction of the Fusion Multi-Modal Imaging Gene 1) in order to reduce the influence of fusion expression of multiple imaging genes on protein folding and spatial conformation, and maintain the activity of each protein, Nanoluc, mRuby2 and Gcamp6f are respectively connected by flexible polypeptide sequences S-L-D-S (SEQ ID NO.8) and G-S-S-G (SEQ ID No.9) as linkers, and fusion expression of multiple imaging genes is as shown in FIG. 1.
2) Nanoluc gene and mRuby2 gene are obtained by gene synthesis, respectively, the tail stop codon is removed, BamHI restriction enzyme sequence (GGATCC) is added at the front end of Nanoluc gene, and one S amino acid gene sequence (TCG) and XhoI restriction enzyme sequence (CTCGAG) are added at the end: SalI restriction enzyme sequence (GTCGAC, XhoI homotail enzyme) and one S amino acid (TCG) are successively added to the front end of mRuby2. One G amino acid sequence (GGA) and an XbaI restriction enzyme sequence (TCTAGA) are added to the back end of mRuby2.
3) The plasmid carrying Gcamp6f gene comes from Beijing Maijin Biology Science and Technology Co., Ltd., and the Gcamp6f gene is amplified by PCR. In the primer design, one G amino acid (GGA) and a SpeI restriction site (XbaI homotail enzyme) are successively added at the front end of the gene, and a PmeI restriction site sequence is added at the end of the gene. The primer sequence is as follows:

SEQ ID NO.4: upstream primer:

<u>actagt</u>ggaatgggttctctctctctctctctctctctctctgt (the underlined part is SpeI restriction site and G amino acid codon);

SEQ ID NO.5: downstream primer:
gtttaaactcacttcgctgtcatttgta (the underlined part is PmeI restriction site sequence).
4) The XhoI restriction site at the tail end of Nanoluc and the SalI restriction site at the front end of mRuby2 are used to cut the Nanoluc gene and mRuby2 gene by XhoI enzyme and SalI enzyme (purchased from Thermo Company) respectively, and the cut products are purified by agarose electrophoresis: by using the characteristics that XhoI and SalI are homotail enzymes, the above-mentioned enzyme-digested product of Nanoluc gene are connected with the enzyme-digested product of mRuby2: the ligation product is amplified by PCR, amplification product are recycled and purified by agarose gel electrophoresis, the purified product is further ligated to a T vector (purchased from Takara Company) and DH5α competent cells (purchased from Bome Company) are transformed.
5) The transformed cells are coated on LB solid culture medium containing ampicillin and cultured in an incubator at 37° C. for 24 hours: about 5 mL of LB liquid medium containing ampicillin is added into sterile test tubes which are numbered respectively, bacterial monoclones are selected, each clone is transferred to a test tube, and cultured and amplified; 1 mL of bacterial liquid is taken from each of the above test tubes, submitted to a sequencing company for sequencing to determine the bacterial liquid of Nanoluc-S-L-D-S-mRuby2 with completely correct gene sequence, amplify and extract the plasmid, and store for later use.
6) PCR amplification of Nanoluc-S-L-D-S-mRuby2 gene, SEQ ID NO.6: upstream primer:

ggatccatggtcttcacactcgaagatttcgt (the underlined part is BamHI restriction sequence), SEQ ID NO.7: downstream primer:

tctagatcccttgtacagctcgtccatcccaccac (the underlined part is XbaI restriction site);
XbaI enzyme (Thermo Company) is used to treat PCR products, while SpeI enzyme (purchased from Thermo Company) is used to treat Gcamp6f gene amplification products, and the enzyme-digested products are purified by agarose gel electrophoresis.
7) Accord to the same method as in the previous step 4)-5), a bacterial solution containing the fusion gene Nanoluc-S-L-D-S-mRuby2-G-S-S-G-Gcamp6f with completely correct sequence is obtained through ligation, transformation, sequencing and the like, and the plasmid (T vector plasmid) is amplified and extracted, and stored for later use. As shown in SEQ ID NO.1, the sequence of fusion imaging gene is constructed.

(2) Construction of Lentiviral Expression Plasmid Carrying Fusion Imaging Gene
1) taking the pLenti-EF1α-FH-CMV-CopGFP&Puro plasmid from Weizhen Bioscience Incorporation as the skeleton (as shown in FIG. 2, the nucleotide sequence is shown in SEQ ID NO.3), and removing the EF-1α promoter in the original plasmid by double restriction endonuclease digestion with SphI and BamHI (purchased from Thermo Company);
2) inserting the human ubiquitin promoter hUbc into the skeleton plasmid through enzyme connection to replace the EF-1α promoter, and obtaining the pLenti-Ubc-FH-CMV-CopGFP&Puro plasmid;
3) transforming DH5α competent cells with enzyme ligation products: coating the transformed cells on LB solid medium containing ampicillin and culturing in an incubator at 37° C. for 24 hours: add about 5 mL of LB liquid medium containing ampicillin into sterile test tubes, numbering them respectively, selecting bacterial monoclones, transferring each clone to a test tube, and culturing and amplifying; taking 1 mL of the bacterial solution of each test tube, submitting it to a sequencing company for sequencing to determine the bacterial solution with completely correct gene sequence, amplifying, extracting plasmid, and storing it for later use;
4) using BamHI and PmeI double enzyme digestion to remove the sequence from Ubc downstream to Puro gene site in pLenti-Ubc-FH-CMV-CopGFP&Puro plasmid, that is, the nucleotide sequence from 3826 to 6112 in the nucleotide sequence shown in SEQ ID NO.3;
5) using the same restriction sites (BamHI and PmeI) at both ends of the NanoLuc-mRuby2-Gcamp6 fusion imaging gene prepared above to digest the T vector plasmid containing the above-mentioned fusion gene, so as to obtain the fusion gene fragment, and then connecting the fusion gene by DNA ligase (purchased from Promega Company), and inserting the fusion gene into the downstream of Ubc promoter in the above-mentioned restriction plasmid to obtain pLenti-Ubc-Nanoluc-mRuby2-Gcamp6f plasmid;
6) as in the above step 3) to obtain the plasmid with completely correct gene sequence and store for later use.

As shown in FIG. 3, the structural map of lentiviral expression plasmid carrying fusion gene is successfully constructed, and the sequence of plasmid gene is shown in SEQ ID NO.1

(3) Preparation of Lentivirus Carrying the Fusion Multi-Modal Imaging Gene

Figure 4A:
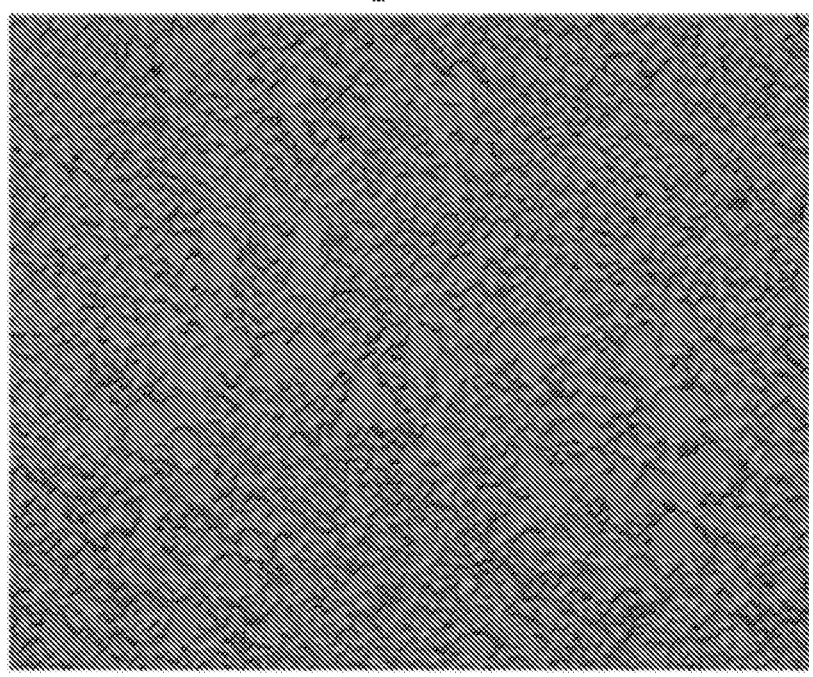
FIG. 4A is a bright field image under phase contrast microscope after the lentiviral expression plasmid carrying the fusion multi-modal imaging genes constructed in an embodiment of the disclosure (the total length of the plasmid <10000 bp) and the packaging plasmid co-transfect 293T cells.
Figure 4B:
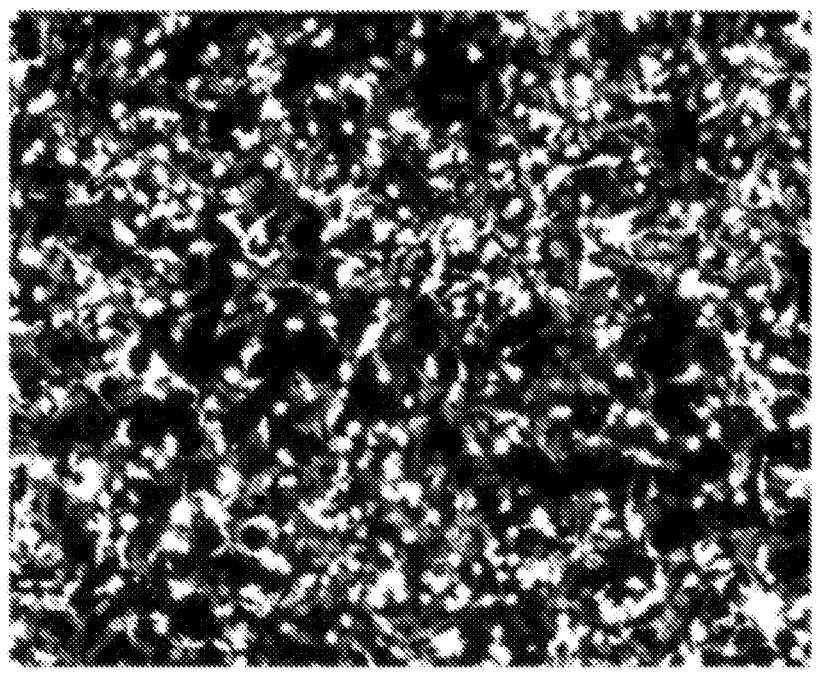
FIG. 4B is a fluorescent microscope image after the lentiviral expression plasmid carrying the fusion multi-modal imaging genes constructed in an embodiment of the disclosure (the total length of the plasmid <10000 bp) and the packaging plasmid co-transfect 293T cells.

The above-mentioned pLenti-Ubc-Nanoluc-mRuby2-Gcamp6f plasmid, packaging plasmids PAX2 and PMD2G in the ratio of 3:2:1 are used to co-transfect 293T cells according to the conventional lentivirus packaging method (refer to PLOS One 2013: 8 (6): e66369.). After 48 hours of transfection, the transfection efficiency of fluorescent protein is observed to preliminarily judge the packaging efficiency. The experimental results are shown in FIG. 4A-FIG. 4B. FIG. 4A-FIG. 4B show the efficiency of co-transfecting 293T cells by the modified lentiviral expression plasmid into which the multi-modal imaging gene inserted (the total length of the plasmid is less than 10000 bp) together with the packaging plasmids. Co-transfection of 293T cells by the lentiviral expression plasmid with the multi-modal imaging gene and the packaging plasmids has relatively high transfection efficiency, and from the observation of fluorescence expression rate, the successful transfection rate is 80-90%, suggesting that it has good virus packaging efficiency.

Figure 5A:
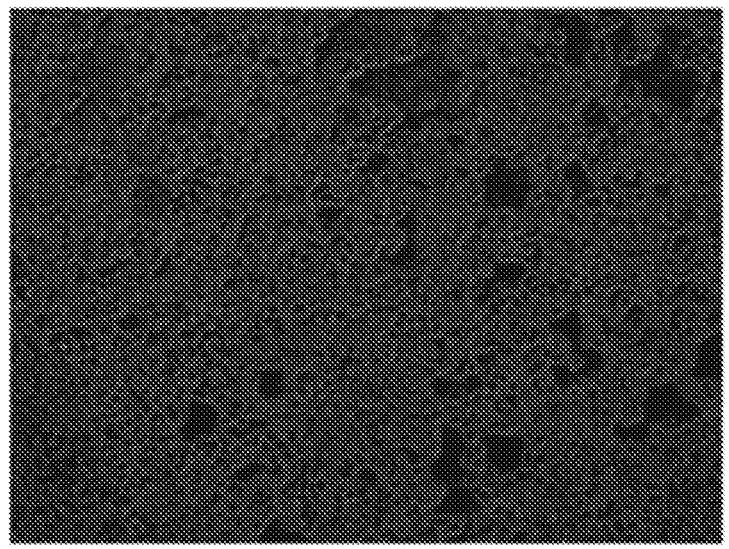
FIG. 5A is a bright field image under phase contrast microscope after conventional lentiviral expression plasmid carrying reporter genes (the total length of the plasmid <10000 bp) and the packaging plasmid co-transfect 293T cells in an embodiment of the disclosure.
Figure 5B:
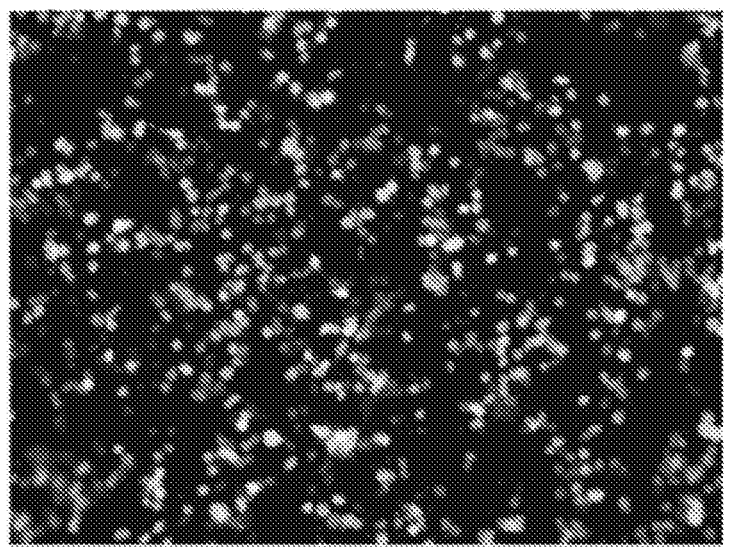
FIG. 5B is a fluorescent microscope image after conventional lentiviral expression plasmid carrying reporter genes (the total length of the plasmid <10000 bp) and the packaging plasmid co-transfect 293T cells in an embodiment of the disclosure.
Figure 6A:
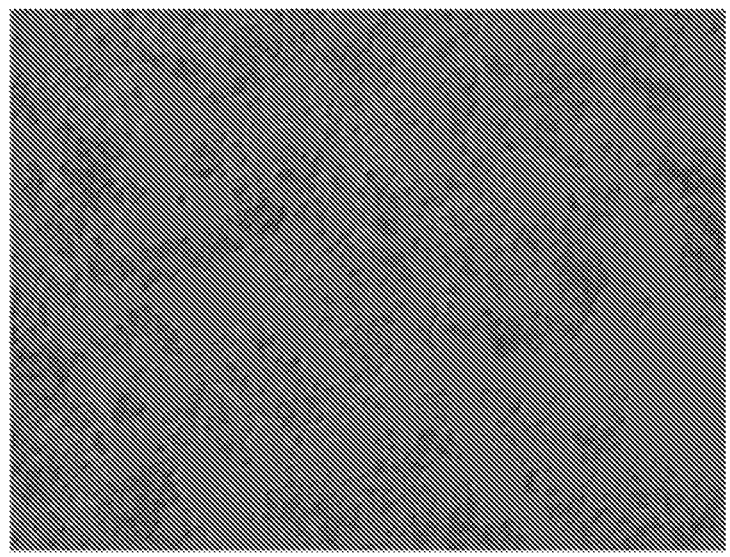
FIG. 6A is a bright field image under phase contrast microscope after the conventional lentiviral expression plasmid carrying multiple imaging genes (the total length of the plasmid >11000 bp) and the packaging plasmid co-transfect 293T cells in an embodiment of the disclosure.
Figure 6B:
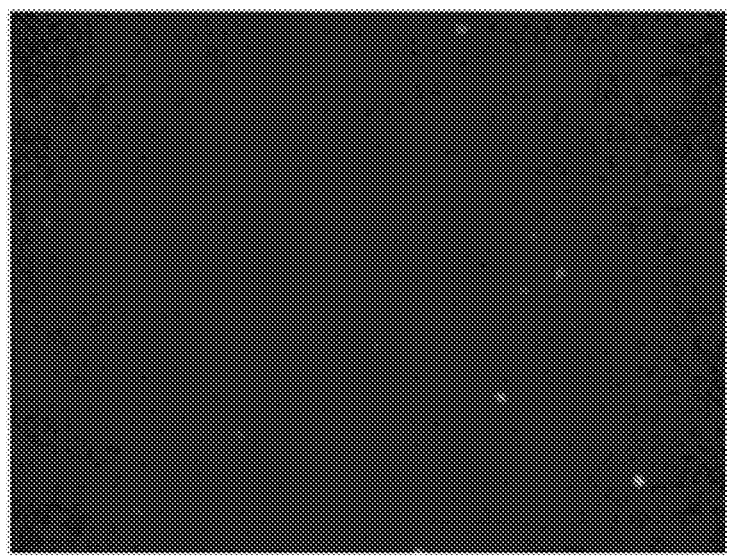
FIG. 6B is a fluorescent contrast microscope image after the conventional lentiviral expression plasmid carrying multiple imaging genes (the total length of the plasmid >11000 bp) and the packaging plasmid co-transfect 293T cells in an embodiment of the disclosure.

At the same time, the conventional lentiviral expression plasmid carrying a single fluorescent protein (only carrying mRuby2 gene) and the conventional lentiviral expression plasmid carrying a plurality of imaging genes with a long length (using pLenti-EF1α-FH-CMV-CopGFP&Puro plasmid before modification to insert the fusion multi-modal imaging gene in embodiment 1 of the present disclosure directly) are used as controls to compare the virus packaging efficiency. FIG. 5A-FIG. 5B show the efficiency of co-transfection of 293T cells by the conventional lentiviral expression plasmid into which the single reporter gene is inserted (the total length of the plasmid is less than 10000 bp) together with the packaging plasmids. It can be seen from FIG. 5A-FIG. 5B that the efficiency of co-transfection of 293T cells is about 80-90% when the conventional lentivirus is packaged, which is equivalent to the efficiency of the modified plasmid packaging virus inserted with multi-modal imaging gene. FIG. 6A-FIG. 6B show the efficiency of co-transfection of 293T cells by the general lentiviral expression plasmid into which the fusion multi-modal imaging gene is inserted (the total length of the plasmid is >11000 bp), together with the packaging plasmids.

As shown in FIG. 4A-FIG. 4B, the co-transfection efficiency of the modified plasmid carrying the fusion gene in the embodiment of the present disclosure is 80-90%, which is equivalent to that of the conventional plasmid carrying a single fluorescent protein as shown in FIG. 5A-FIG. 5B, suggesting that both the lentiviral plasmid inserted with multiple reporter genes and the conventional lentiviral plasmid have higher lentiviral packaging efficiency, while as shown in FIG. 6A-FIG. 6B, the co-transfection packaging efficiency of the conventional lentiviral plasmid inserted with multiple reporter genes and with long length is very low, about 10-20%. The lentiviral expression plasmid with long length deadly influences the virus packing rate. The results show that it is necessary to modify the conventional lentivirus plasmid skeleton, provide space for the longer fusion gene probe and reduce the total length of plasmid, so as to maintain the packaging efficiency of lentivirus. The deletion and modification of plasmid skeleton in the disclosure improves the length of foreign gene insertion and maintains plasmid activity.

Figure 7A:
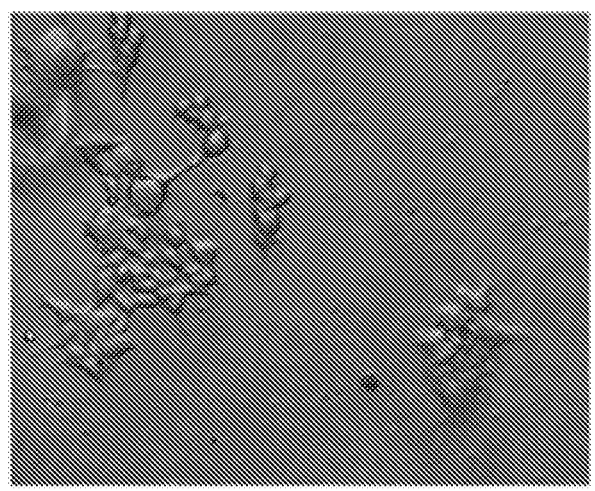
FIG. 7A is a bright field image under phase contrast microscope of lentivirus particles carrying fusion multi-modal imaging genes transfected into 293T cells in an embodiment of the present disclosure.
Figure 7B:
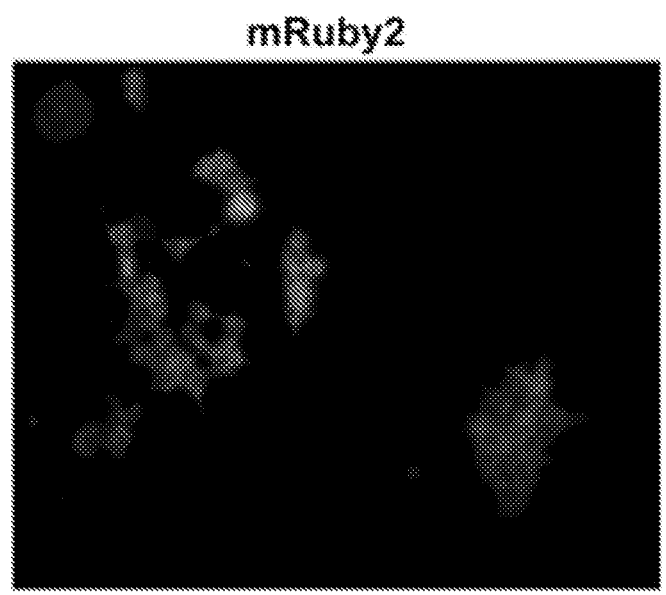
FIG. 7B shows an expression of mRuby2 by fluorescent microscope after lentivirus particles carrying the fusion multi-modal imaging genes transfects 293T cells in an embodiment of the present disclosure.
Figure 7C:
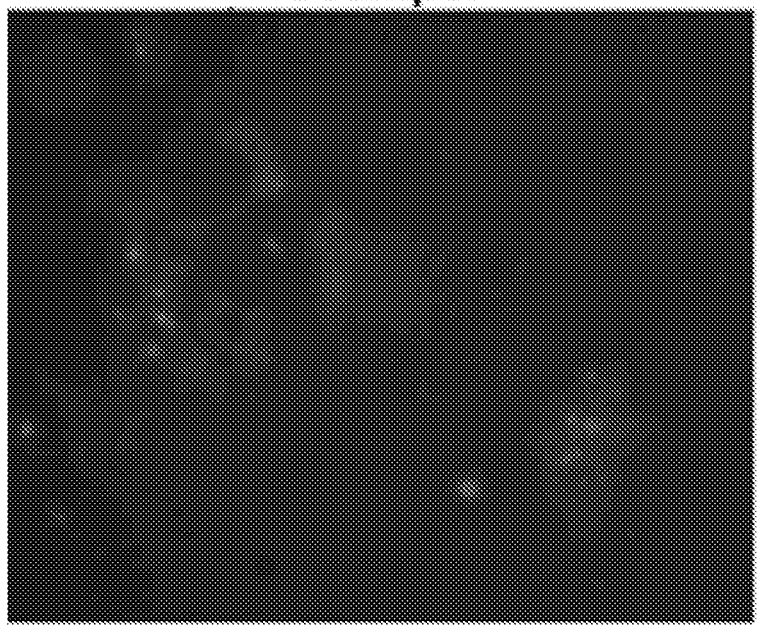
FIG. 7C shows an expression of Gcamp6f by fluorescent microscope after lentivirus particles carrying the fusion multi-modal imaging genes transfects 293T cells in an embodiment of the present disclosure.

After lentivirus particles are collected, 293T cells are marked with transgene by conventional lentivirus infection. The experimental results are shown in FIG. 7A-FIG. 7C. As can be seen from FIG. 7A-FIG. 7C, 293T cells are successfully infected by the virus and expressed by mRuby2 fluorescent protein, while Gcamp6f is basically in a non-fluorescent state in a conventional environment without calcium ions. It is proves that lentivirus has good activity, and the normal activity of each protein is maintained by connecting the fusion gene with the peptide chain of S-L-D-S and G-S-S-G, suggesting that lentivirus particles carrying multi-modal imaging gene prepared by the disclosure have good activity.

Figure 8A:
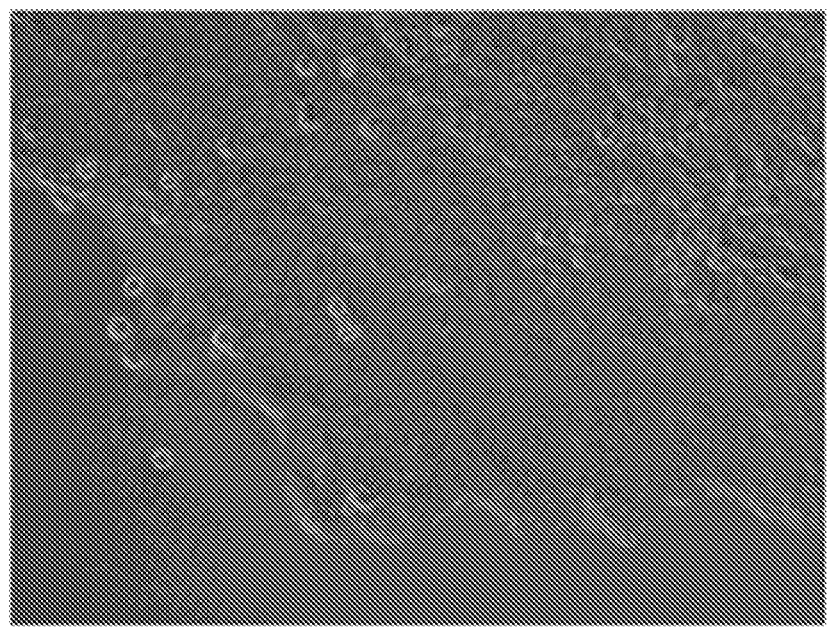
FIG. 8A is a bright field image of human embryonic stem cells (hESC) under phase contrast microscope transfected and marked with lentivirus particles carrying fusion multi-modal imaging genes in an embodiment of the disclosure.
Figure 8B:
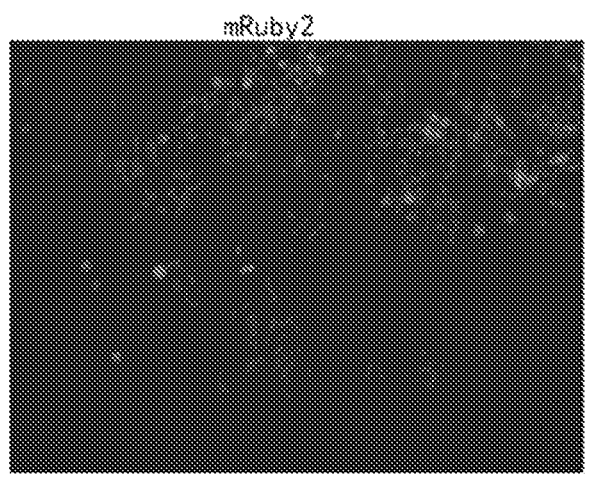
FIG. 8B is a fluorescent microscope image of human embryonic stem cells (hESC) transfected and marked with lentivirus particles carrying fusion multi-modal imaging genes in an embodiment of the disclosure.

Embodiment 2: Application of Fusion Multi-Modal Imaging Gene in Human Pluripotent Stem Cells (1) Multi-Modal Imaging Gene Marker of Human Embryonic Stem Cells (hESC)

h1ESC (presented by Professor Cao Nan of Sun Yat-sen University or purchased from American ATCC) is transfected by the lentivirus particles carrying the fusion gene probe mentioned above through infection method of cells by conventional lentiviruses (refer to PLOS One. 2013: 8 (6): e66369.), and the positive clones are isolated and amplified by the method described by the patent (ZL201911133148.1). The experimental results are shown in FIG. 8A-FIG. 8B. From FIG. 8A-FIG. 8B, it can be seen that the lentivirus particles carrying the fusion multi-modal imaging gene prepared by the disclosure successfully transfect hESC, and the expression of mRuby2 is observed, thus successfully obtaining the hESC cell line marked by the fusion imaging gene. It is suggested that the lentivirus particles carrying multi-modal imaging gene prepared by the disclosure have good activity.

(2) Multi-Modal Imaging Gene Marker of Human Induced Pluripotent Stem Cells (hiPSC)

Figure 9A:
FIG. 9A is a bright field image of human induced pluripotent stem cells (hiPSC) under phase contrast microscope transfected and marked with lentivirus particles carrying fusion multi-modal imaging genes in an embodiment of the disclosure.
Figure 9B:
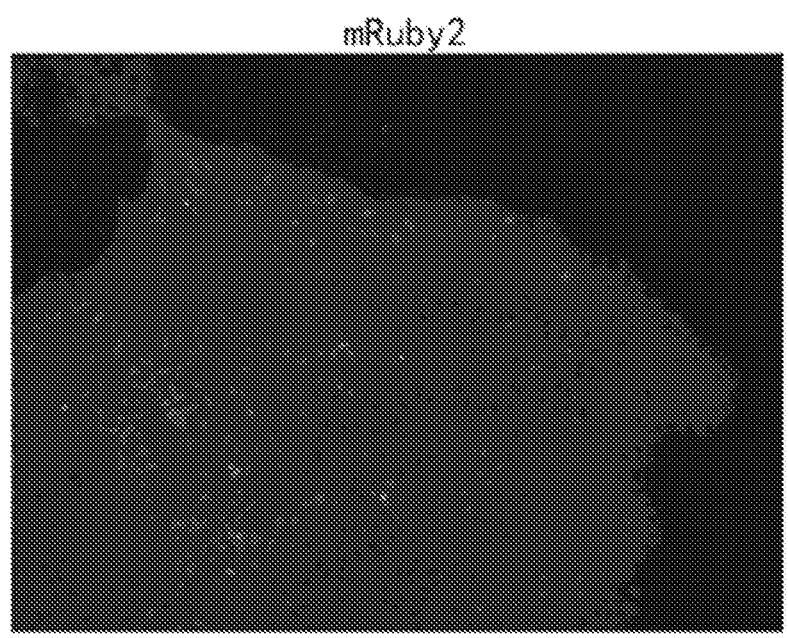
FIG. 9B is a fluorescent microscope image of hiPSC transfected and marked with lentivirus particles carrying fusion multi-modal imaging genes in an embodiment of the disclosure.

The lentivirus particles carrying the fusion gene probe is used to transfect hiPSC0100 (from Shanghai Stem Cell Bank of Chinese Academy of Sciences) through infection method of cells by conventional lentiviruses (refer to PLOS One. 2013: 8 (6): e66369.), and the positive clones are isolated for amplification by the method described by patented (ZL201911133148.1). The experimental results are shown in FIG. 9A-FIG. 9B. From FIG. 9A-FIG. 9B, it can be seen that the lentivirus particles carrying the fusion multi-modal imaging gene prepared by the disclosure successfully transfects hiPSC, and the expression of mRuby2 is observed, and the hiPSC cell line marked by the fusion imaging gene is successfully obtained. It is suggested that the lentivirus particles carrying multi-modal imaging gene prepared by the disclosure have good activity.

(3) Multi-Modal Imaging Detection of Human Pluripotent Stem Cells

Figure 10A:
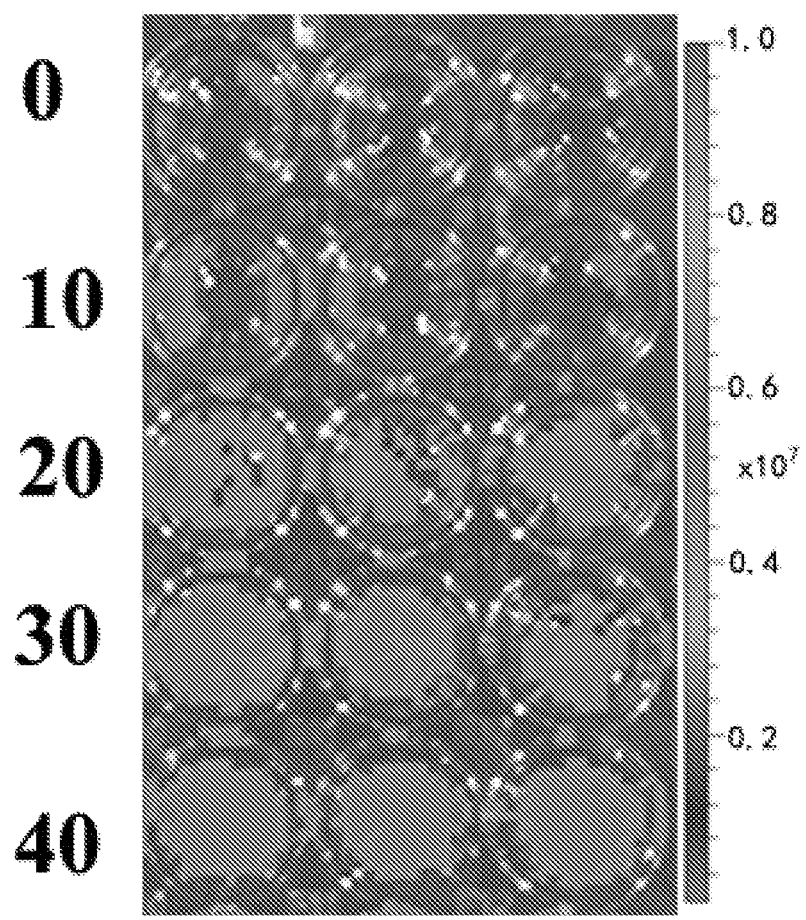
FIG. 10A is a bioluminescence imaging picture.
Figure 10B:
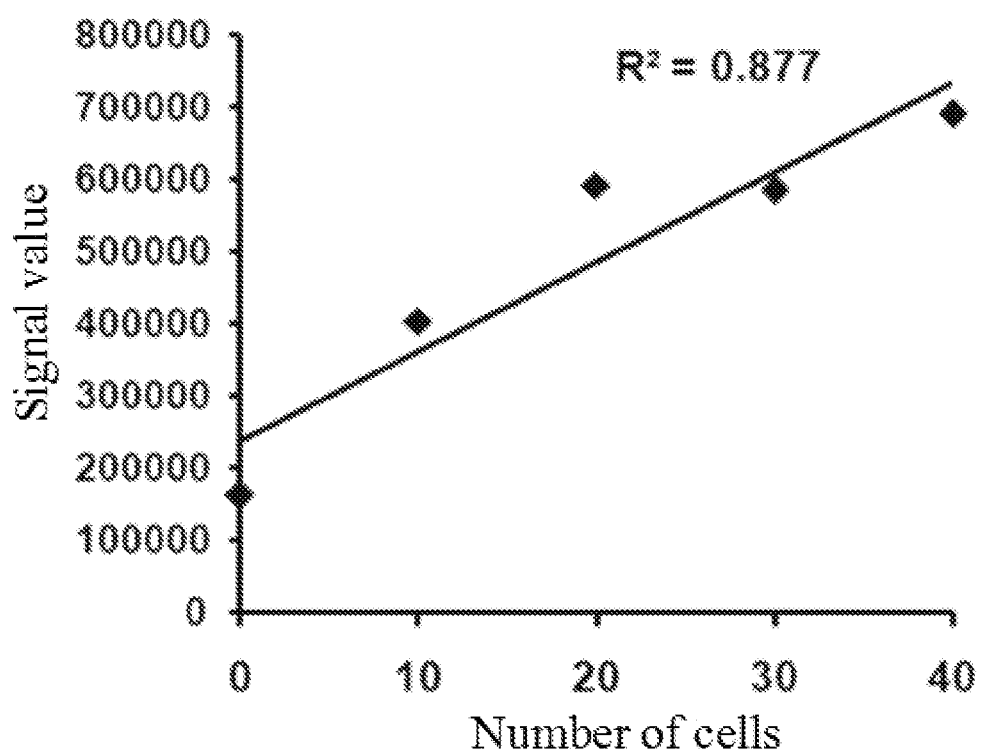
FIG. 10B is the relationship between fluorescence signal value and the number of cells.
Figure 11A:
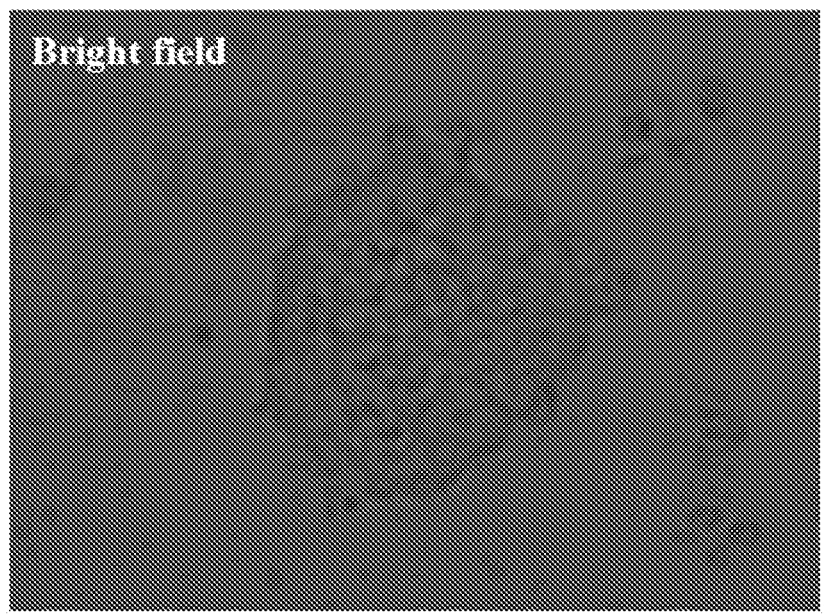
FIG. 11A is a morphological image of hiPSC marked by fusion multi-modal imaging genes in an embodiment of the present disclosure.
Figure 11B:
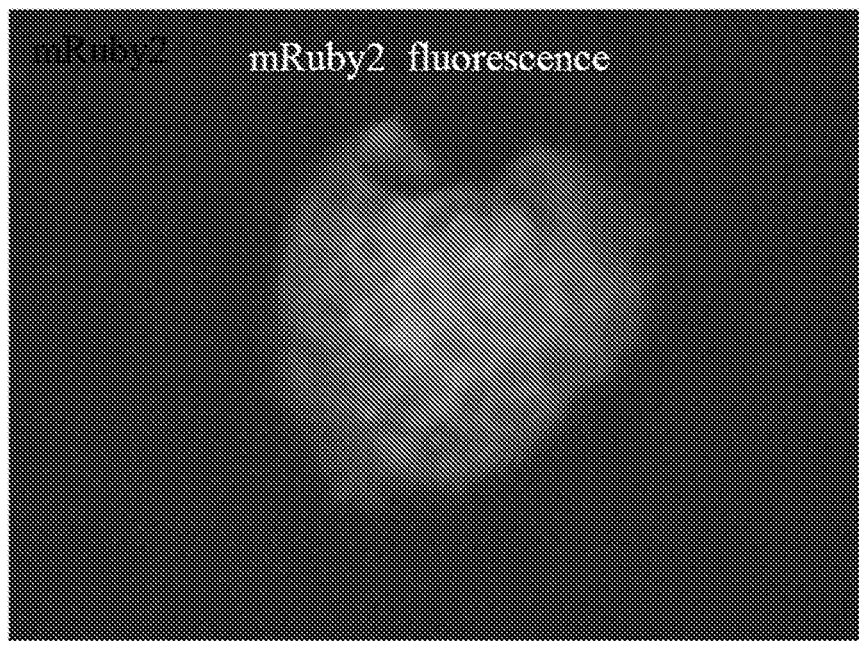
FIG. 11B fluorescence imaging of hiPSC reporter gene mRuby2 marked by fusion multi-modal imaging genes in an embodiment of the present disclosure.
Figure 11C:
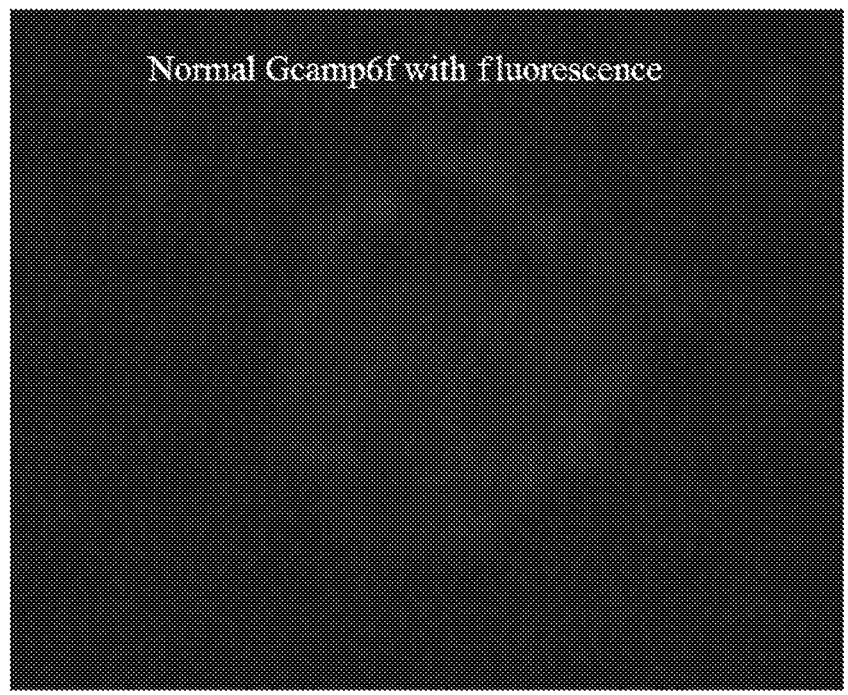
FIG. 11C shows that hiPSC reporter gene Gcamp6f marked by fusion multi-modal imaging genes in an embodiment of the present disclosure has no fluorescence under normal conditions.
Figure 11D:
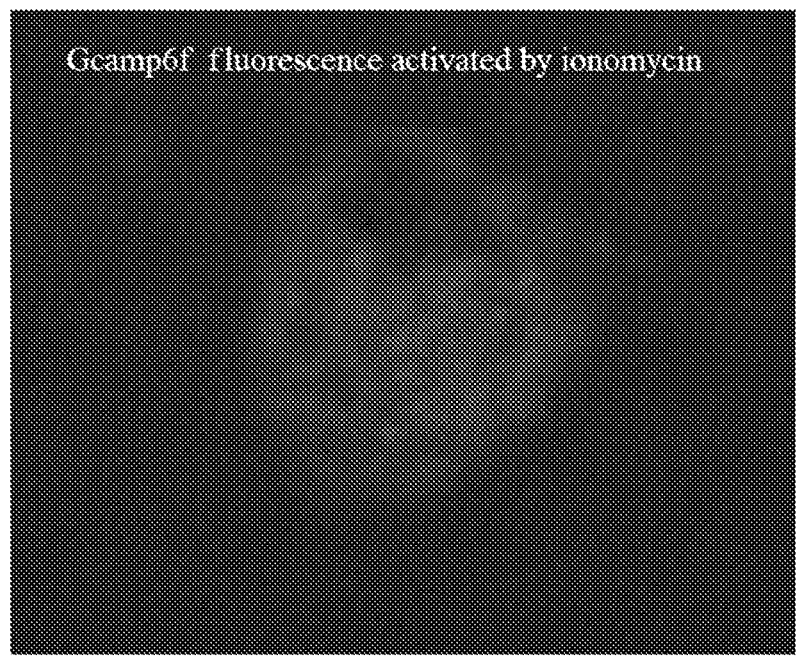
FIG. 11D shows the fluorescence signal of the hiPSC reporter gene Gcamp6f marked by the fusion multi-modal imaging genes under the treatment of ionomycin in an embodiment of the present disclosure.

Quantitative imaging, morphological imaging and calcium activity functional imaging are carried out by using hiPSC marked by fusion imaging gene. The basic method of quantitative imaging is to collect marked hiPSC with good growth state, disperse it into single cell suspension, dilute it to 0, 10, 20, 30, 40 iPSC per 100 μL of culture solution, 100 μL of the above gradient cell suspension is add to a 96-well culture plate, Nanoluc substrate solution is added according to the instructions of the kit (from Promega, article number N1110), and an in vivo imager (Invitrogen in vivo) is used for detecting fluorescence signal. The experimental results are shown in FIG. 10A-FIG. 10B, in which FIG. 10A is a bioluminescence imaging picture, and FIG. 10B is the relationship between fluorescence signal value and the number of cells. It shows that bioluminescence imaging based on Nanoluc may quantify the number of cells, and the sensitivity may reach less than 10 cells. The results of morphological imaging (mRuby2) and calcium activity functional imaging (Gcamp6f) are shown in FIG. 11A-FIG. 11D. The typical morphology of cells are observed by fluorescent microscope imaging by using mRuby2, and the morphology of marked cells are detected after cell transplantation: at the same time, it is observed that Gcamp6f is in a state of no or low fluorescence under normal conditions. By adding 10 μM ionomycin (purchased from Sigma Company) to stimulate calcium activity, the fluorescence of Gcamp6f is significantly activated, indicating that the fusion imaging gene is capable of cellular calcium activity imaging.

Figure 12A:
FIG. 12A shows a neural network morphology formed by a differentiation of hiPSC marked by the fusion multi-modal imaging genes in an embodiment of the present disclosure.
Figure 12B:
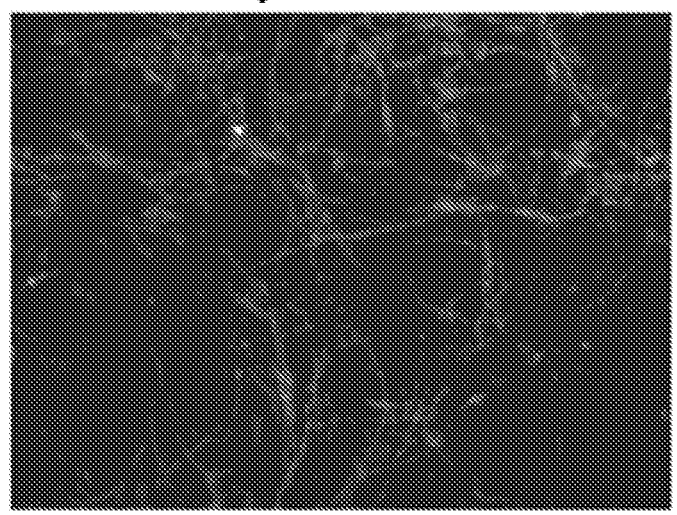
FIG. 12B fluorescence maintenance of mRuby2 reporter gene in neural network formed by differentiation of hiPSC marked by fusion multi-modal imaging genes in an embodiment of the present disclosure.
Figure 13A:
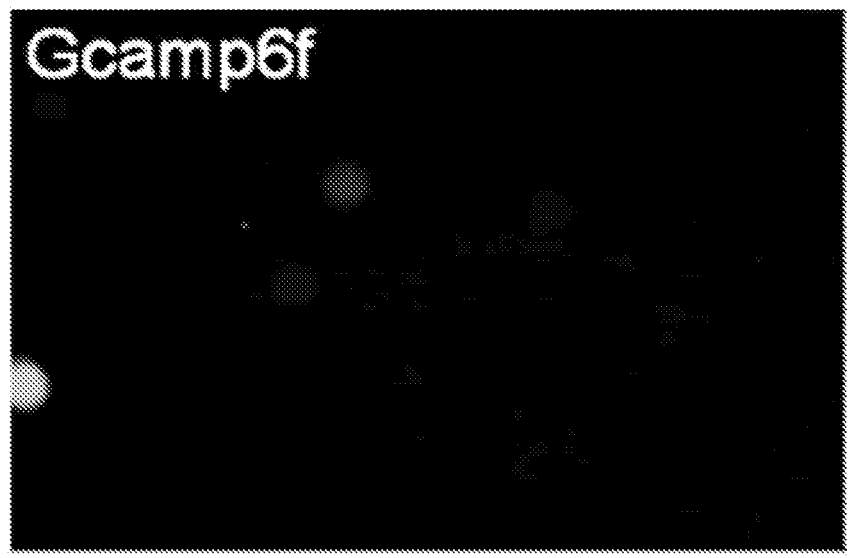
FIG. 13A shows that the Gcamp6f reporter gene in the neural network formed by the differentiation of hiPSC marked by the fusion multi-modal imaging genes has no fluorescence under normal conditions in an embodiment of the present disclosure.
Figure 13B:
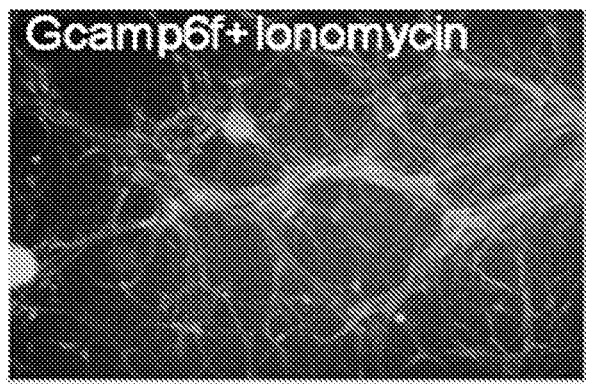
FIG. 13B shows that the Gcamp6f reporter gene in the neural network formed by the differentiation of hiPSC marked by the fusion multi-modal imaging genes generates fluorescence under the action of ionomycin (corresponding to the neural network of FIG. 13A) in an embodiment of the present disclosure.
Figure 13C:
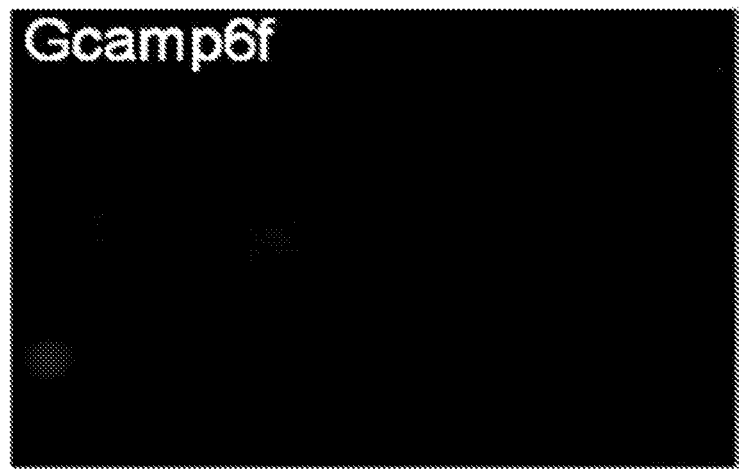
FIG. 13C shows that the Gcamp6f reporter gene in the neural network formed by the differentiation of hiPSC marked by the fusion multi-modal imaging genes has no fluorescence under normal conditions in an embodiment of the present disclosure.
Figure 13D:
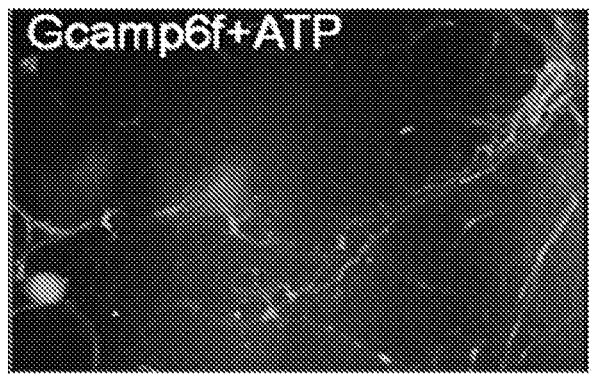
FIG. 13D shows that the Gcamp6f reporter gene in the neural network formed by the differentiation of hiPSC marked by the fusion multi-modal imaging genes generates fluorescence under ATP treatment (corresponding to the neural network of FIG. 13C) in an embodiment of the present disclosure.

Embodiment 3: Application of Fusion Multi-Modal Imaging Gene in Human Pluripotent Stem Cells-Differentiated Cells (1) Morphological Imaging Detection of Nerve Cells Derived from hiPSC According to the existing methods (English book Methods in Molecular Biology, Neural Stem Cells PP 1-7), the hiPSC is differentiated into neural stem cells (NSCs), and then NSC balls are attached to the wall for growth, and the neuron culture medium is used for long-term culture to promote the differentiation into nerve cells. The experimental observation results of morphological imaging of neural network formed by hiPSC differentiation are shown in FIG. 12A-FIG. 12B. It can be seen from FIG. 12A-FIG. 12B that NSC differentiated and cultured for 4 months forms an obvious neural network morphology, and the stable expression of mRuby2 is observed through a fluorescent microscope (purchased from Nikon Company, Ti2-U model), showing a good neural network morphology. It is suggested that multi-modal imaging gene may still maintain stable expression after cell proliferation and nerve differentiation, and may be used for stable imaging tracking of differentiated nerve cells.

(2) Functional Imaging Detection of Calcium Activity in Nerve Cells Derived from hiPSC Using the neural network formed by the above-mentioned hiPSC differentiation, the reaction of Gcamp6f protein is observed under the normal environment and the stimulation of ionomycin and ATP respectively. The experimental results of calcium activity functional imaging of neural network formed by hiPSC differentiation are shown in FIG. 13A-FIG. 13D. As shown in FIG. 13A-FIG. 13D, the activation of fluorescence signal is observed under the stimulation of ionomycin and ATP (purchased from Sigma Company), which indicates that the fusion gene probe maintains good activity in hiPSC differentiation and may be used for imaging calcium activity of differentiated cells.

Figure 14:
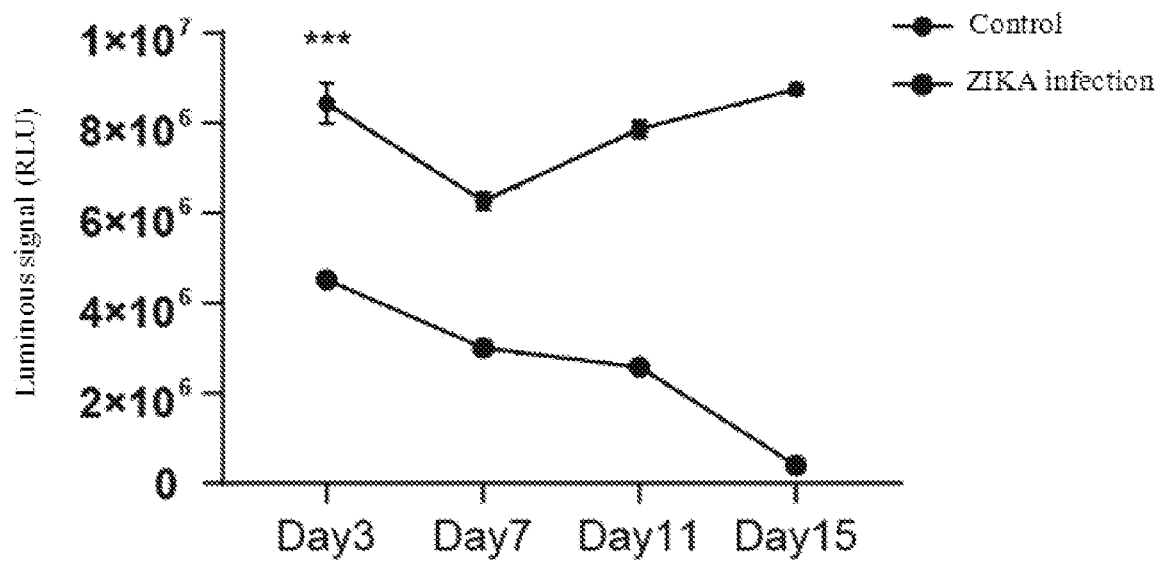
FIG. 14 is a quantitative imaging of cell viability (representing the number of living cells) of brain-like organs cultivated by hiPSC marked by fusion multi-modal imaging gene during ZIKA infection in an embodiment of the present disclosure.
Figure 15A:
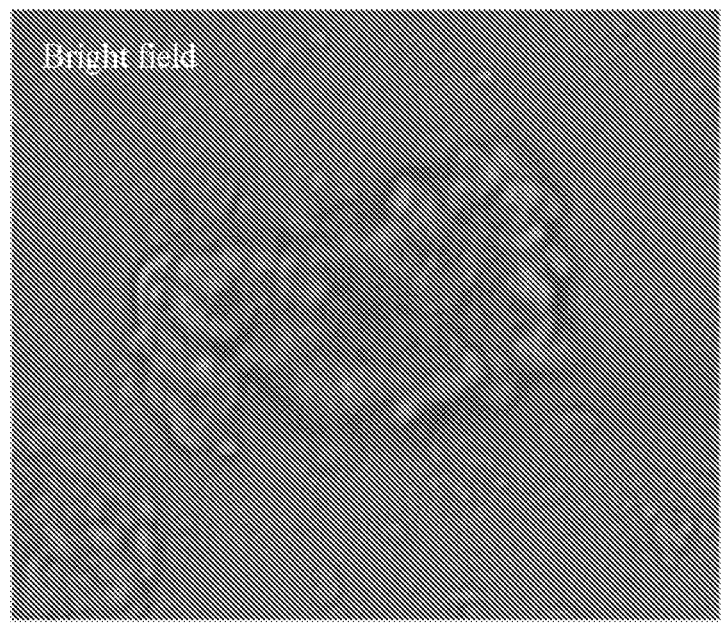
FIG. 15A is a phase contrast microscope bright-field image of hiPSC differentiated cardiomyocytes marked with fusion multi-modal imaging genes in an embodiment of the present disclosure.
Figure 15B:
FIG. 15B is mRuby2 fluorescence imaging of hiPSC differentiated cardiomyocytes marked with fusion multi-modal imaging genes in an embodiment of the present disclosure.
Figure 15C:
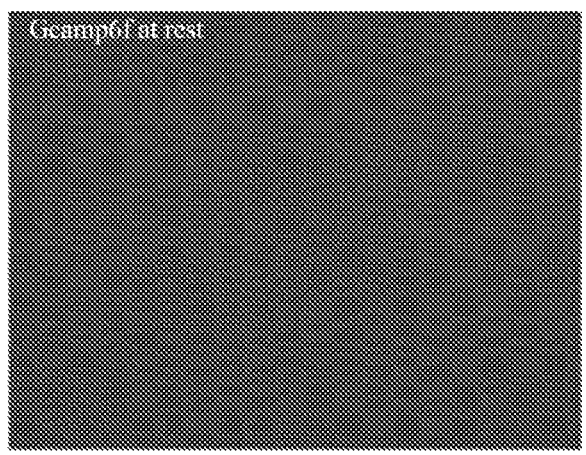
FIG. 15C shows that the reporter gene Gcamp6f in the hiPSC differentiated cardiomyocytes marked by the fusion multi-modal imaging genes has no fluorescence at rest in an embodiment of the present disclosure.
Figure 15D:
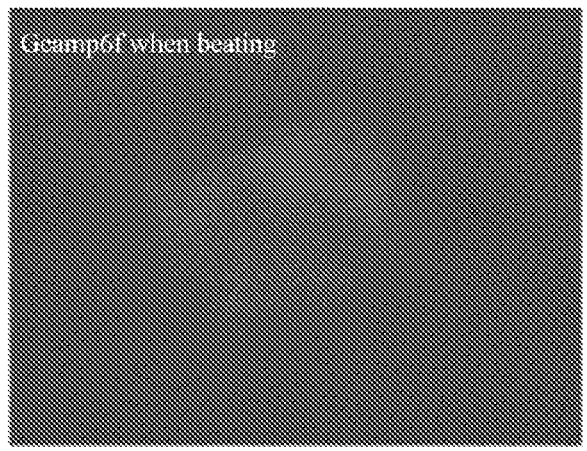
FIG. 15D shows that the reporter gene Gcamp6f in the hiPSC differentiated cardiomyocytes marked by the fusion multi-modal imaging genes generates fluorescence under the beating state of the cells in an embodiment of the present disclosure.

(3) Real-Time Quantitative Imaging Detection of Cell Viability in Brain-Like Organs Derived from hiPSC According to the method reported in the literature (J. Vis. Exp. 2017; 127: e56404), iPSC marked by fusion gene probe is cultivated to form brain-like organs as the infection model of ZIKA. Virus infection may lead to nerve cells and neural stem cells to die, but it can't be distinguished by conventional morphological observation. Previous studies have used invasive sampling to detect. Using Nanoluc protein, the cell viability is detected non-invasively and continuously at different time points after ZIKA infection, and the experimental results of cell number imaging of brain-like organs cultivated by hiPSC during ZIKA infection are shown in FIG. 14. As shown in FIG. 14, three days after ZIKA infection, the cells in brain-like organs die obviously, and then the cell vitality continues to decline during the infection process, thus realizing continuous, visual and quantitative imaging of the cell vitality in the same specimen.

Figure 16:
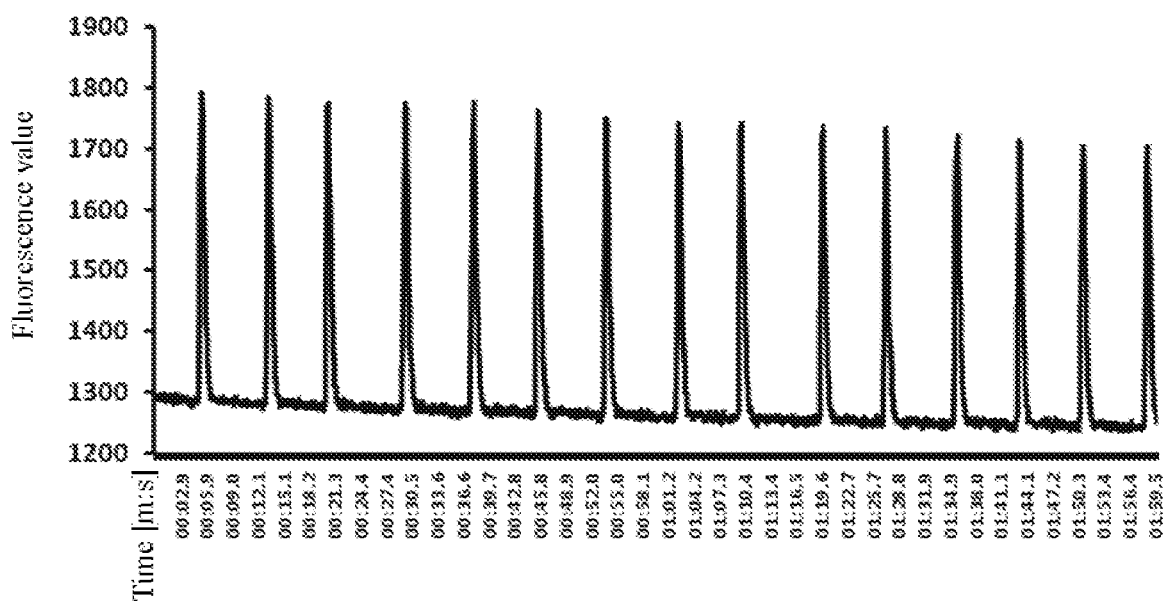
FIG. 16 is a real-time imaging of calcium activity of hiPSC-differentiated cardiomyocytes marked by fusion multi-modal imaging gene during rhythm fluctuation in an embodiment of the present disclosure.

(4) Real-Time Imaging Detection of Calcium Activity in Myocardial Cells Derived from hiPSC 1) fusing gene-marked hiPSC cells, culturing until 80% confluence;
2) replacing by RPMI1640 medium (purchased from Gibco company), adding insulin-free B27 (1×, purchased from Gibco company) and 6 uM CHIR99021 (purchased from Merck company), and culturing for 48 hours;
3) replacing by fresh RPMI1640 medium, adding insulin-free B27 (1×), and culturing for 24 hours;
4) replacing by RPMI1640 medium, adding insulin-free B27 (1×) and 6 uM IWR-1 (purchased from Merck company), and culturing for 48 hours;
5) replacing by RPMI1640 medium, adding insulin-free B27 (1×) and culturing for 48 hours;
6) replacing RPMI1640 medium, adding B27 (1×) containing insulin, and changing the liquid every three days. The appearance of pulsatile cells is observed during culture;
7) using living cell workstation (purchased from Nikon Company) to observe the expression of mRuby2: at the same time, recording the fluorescence changes of Gcamp6f in real time. The experimental results of morphological imaging and calcium activity functional imaging of hiPSC differentiated cardiomyocytes are shown in FIG. 15A-FIG. 15D. The stable expression of mRuby2 is observed by using marked iPSC differentiated cardiomyocytes, and at the same time, it can be observed from Gcamp6f imaging that cardiomyocytes have no fluorescence at rest and activate fluorescence sensitively when beating. Furthermore, in the process of myocardial beating, the rhythm change of fluorescence signal may be detected when myocardial cells beat rhythmically. The experimental results of continuous imaging of calcium activity of hiPSC differentiated nerve cells marked by multi-modal imaging gene are shown in FIG. 16. As shown in FIG. 16, the marked iPSC is used to differentiate and form cardiomyocytes, which are accompanied by the rhythm change of calcium activity in the beating process, and the Gcamp6f and the living cell workstation are used for real-time imaging, so that the rhythm change of fluorescence signals accompanied by the rhythm fluctuation of cardiomyocytes may be observed, which indicates that the multi-modal imaging gene in the disclosure may be used for high-sensitivity and real-time imaging detection of cellular calcium activity.

SEQUENCE LISTING

```
Sequence total quantity: 9
SEQ ID NO: 1            moltype = DNA   length = 2615
FEATURE                 Location/Qualifiers
source                  1..2615
                        mol_type = other DNA
                        organism = synthetic construct
SEQUENCE: 1
ggatccatgg tcttcacact cgaagatttc gttggggact ggcgacagac agccggctac   60
aacctggacc aagtccttga acagggaggt gtgtccagtt tgtttcagaa tctcggggtg  120
tccgtaactc cgatccaaag gattgtcctg agcggtgaaa atgggctgaa gatcgacatc  180
catgtcatca tcccgtatga aggtctgagc ggcgaccaaa tgggccagat cgaaaaaatt  240
tttaaggtgg tgtaccctgt ggatgatcat cactttaagg tgatcctgca ctatggcaca  300
ctggtaatcg acggggttac gccgaacatg atcgactatt tcggacggcc gtatgaaggc  360
atcgccgtgt tcgacggcaa aaagatcact gtaacaggga ccctgtggaa cggcaacaaa  420
attatcgacg agcgcctgat caaccccgac ggctccctgc tgttccgagt aaccatcaac  480
ggagtgaccg gctggcggct gtgcgaacgc attctggcgt cgctcgactc gatggtgtct  540
aagggcgaag agctgatcaa ggaaaatatg cgtatgaagg tggtcatgga aggttcggtc  600
aacggccacc aattcaaatg cacaggtgaa ggagaaggca atccgtacat gggaactcaa  660
accatgagga tcaaagtcat cgagggagga ccctgccat ttgcctttga cattcttgcc  720
acgtcgttca tgtatggcag ccgtactttt atcaagtacc cgaaaggcat tcctgatttc  780
tttaaacagt ccttttcctga gggttttact tgggaaagag ttacgagata cgaagatggt  840
ggagtcgtca ccgtcatgca ggacaccagc cttgaggatg gctgtctcgt ttaccacgtc  900
```

-continued

```
caagtcagag gggtaaactt tccctccaat ggtcccgtga tgcagaagaa gaccaagggt    960
tgggagccta atacagagat gatgtatcca gcagatggtg gtctgagggg atacactcat   1020
atggcactga aagttgatgg tggtggccat ctgtcttgct ctttcgtaac aacttacagg   1080
tcaaaaagaa ccgtcgggaa catcaagatg cccggtatcc atgccgttga tcaccgcctg   1140
gaaaggttag aggaaagtga caatgaaatg ttcgtagtac aacgcgaaca cgcagttgcc   1200
aagttcgccg ggcttggtgg tgggatggac gagctgtaca agggatctag tggaatgggt   1260
tctcatcatc atcatcatca tggtatggct agcatgactg gtggacagca aatgggtcgg   1320
gatctgtacg acgatgacga taaggatctc gccaccatgg tcgactcatc ccgtcgtaag   1380
tggaataaga caggtcacgc agtcagagct ataggtcggc tgagctcact cgagaacgtc   1440
tatatcaagg ccgacaagca gaagaacggc atcaaggcga acttcaagat ccgccacaac   1500
atcgaggacg gcggcgtgca gctcgcctac cactaccagc agaacacccc catcggcgac   1560
ggccccgtgc tgctgcccga caaccactac ctgagcgtgc agtccaaact ttcgaaagac   1620
cccaacgaga agcgcgatca catggtcctg ctggagttcg tgaccgccgc cgggatcact   1680
ctcggcatgg acgagctgta caagggcggt accggagggg gcatggtgag caagggcgag   1740
gagctgttca ccggggtggt gcccatcctg gtcgagctgg acggcgacgt aaacggccac   1800
aagttcagcg tgtccggcga gggtgagggc gatgccacct acggcaagct gaccctgaag   1860
ttcatctgca ccaccggcaa gctgcccgtg ccctggccca ccctcgtgac cacccctgacc   1920
tacggcgtgc agtgcttcag ccgctacccc gaccacatga agcagcacga cttcttcaag   1980
tccgccatgc ccgaaggcta catccaggag cgcaccatct tcttcaagga cgacggcaac   2040
tacaagaccc gcgccgaggt gaagttcgag ggcgacaccc tggtgaaccg catcgagctg   2100
aagggcatcg acttcaagga ggacggcaac atcctgggc acaagctgga gtacaacctg   2160
ccggaccaac tgactgaaga gcagatcgca gaatttcatc cctatttgac                2220
aaggacgggg atgggacaat aacaaccaag gagctgggga cggtgatgcg gtctctgggg   2280
cagaacccca cagaagcaga gctgcaggac atgatcaatg aagtagatgc cgacggtgac   2340
ggcacaatcg acttccctga gttcctgaca atgatgcaa gaaaaatgaa atacagggac   2400
acggaagaag aaattagaga agcgttcggt gtgtttgata aggatggcaa tggctacatc   2460
agtgcagcag agcttcgcca cgtgatgaca aaccttggag agaagttaac agatgaagag   2520
gttgatgaaa tgatcaggga agcagacatc gatggggatg gtcaggtaaa ctacgaagag   2580
tttgtacaaa tgatgacagc gaagtgagtt taaac                               2615

SEQ ID NO: 2              moltype = DNA    length = 9300
FEATURE                   Location/Qualifiers
source                    1..9300
                          mol_type = other DNA
                          organism = synthetic construct
SEQUENCE: 2
taacttacgg taaatggccc gcctggctga ccgcccaacg acccccgccc attgacgtca     60
ataatgacgt atgttcccat agtaacgcca tagggactt tccattgacg tcaatggggt    120
gagtatttac ggtaaactgc ccacttggca gtacatcaag tgtatcatat gccaagtacg    180
ccccctattg acgtcaatga cggtaaatgg cccgcctggc attatgccca gtacatgacc    240
ttatgggact ttcctacttg gcagtacatc tacgtattag tcatcgctat taccatggtg    300
atgcggtttt ggcagtacat caatgggcgt ggatagcggt ttgactcacg gggatttcca    360
agtctccacc ccattgacgt caatgggagt ttgttttggc accaaaatca acgggacttt    420
ccaaaatgtc gtaacaactc cgccccattg acgcaaatgg gcggtaggcg tgtacggtgg    480
gaggtctata taagcagcgc gttttgcctg tactgggtct ctctggttag accagatctg    540
agcctgggag ctctctggct aactagggaa cccactgctt aagcctcaat aaagcttgcc    600
ttgagtgctt caagtagtgt gtgcccgtct gttgtgtgac tctggtaact agagatccct    660
cagacccttt tagtcagtgt ggaaaatctc tagcagtggc gcccgaacag ggacttgaaa    720
gcgaaaggga accagagga gctctctcga cgcaggactc ggcttgctga agcgcgcacg    780
gcaagaggcg agggggcggcg actggtgagt acgccaaaaa ttttgactag cggaggctag    840
aaggagagag atgggtgcga gagcgtcagt attaagcggg ggagaattag atcgcgatgg    900
gaaaaaattc ggttaaggcc agggggaaag aaaaaatata aattaaaaca tatagtatgg    960
gcaagcaggg agctagaacg attccgcagtt aatcctggcc tgttagaaac atcagaaggc   1020
tgtagacaaa tactgggaca gctacaacca tccccttcaga caggatcaga agaacttaga   1080
tcattatata atacagtagc aaccctctat tgtgtgcatc aaaggataga gataaaagac   1140
accaaggaag ctttagacaa gatagaggaa gagcaaaaca aaagtaagac caccgcacag   1200
caagcggccg gccgctgatc ttcagacctg gaggaggaga tatgagggac aattggagaa   1260
gtgaattata taaatataaa gtagtaaaaa ttgaaccatt aggagtagca cccaccaagg   1320
caaagaagaa agtggtgcag agagaaaaaa gagcagtggg aatgggagct tgttccttg    1380
ggttcttggg agcagcagga agcactatgg gcgcagcgtc aatgacgctg acggtacagg   1440
ccagacaatt attgtctggt atagtgcagc agcagaacaa tttgctgagg gctattgagg   1500
cgcaacagca tctgttgcaa ctcacagtct ggggcatcaa gcagctccag gcaagaatcc   1560
tggctgtgga agataccta aaggatcaac agctcctggg gatttggggt tgctctggaa    1620
aactcatttg caccactgct gtgccttgga atgctagttg gagtaataaa tctctggaac   1680
agatttggaa tcacacgacc tggatggagt gggacagaga aattaacaat tacacaagct   1740
taatacactc cttaattgaa gaatcgcaaa accagcaaga aaagaatgaa caagaattat   1800
tggaattaga taaatgggca agtttgtgga attggtttaa cataacaaat tggctgtggt   1860
atataaaatt attcataatg atagtaggag gcttggtagg tttaagaata gtttttgctg   1920
tactttctat agtgaataga ttaggcagg gatattcacc attatcgttt cagacccatc   1980
tcccaacccc gaggggaccc gacaggcccg aaggaataga agaagaaggt ggagagagag   2040
acagagacag atccattcga ttagtgaacg gatcggcact cgtgcgcca attctgcaga   2100
caaatgcag tattcatcca caattttaaa agaaaggggg gattgggggg tacagtgca    2160
ggggaaagaa tagtagacat aatagcaaca gacatacaaa ctaaagaatt acaaaaacaa   2220
attacaaaaa ttcaaaattt tcgggttat tacagggaca gcagagatcc agtttggtta   2280
gtaccgggcc cggcctccgc gccgggtttt ggcgcctccc gcgggcgccc cctcctcac    2340
ggcgagcgct gccacgtcag acgaaggcg cagcgagcgt cctgatcctt ccgcccggac   2400
gctcaggaca gcggcccgct gctcataaga ctcggcctta gaaccccagt atcagcagaa   2460
ggacatttta ggacgggact tgggtgactc tagggcactg gttttctttc cagagagcgg   2520
aacaggcgag gaaaagtagt cccttctcgg cgattctgcg gagggatctc cgtggggcgg   2580
```

```
tgaacgccga tgattatata aggacgcgcc gggtgtggca cagctagttc cgtcgcagcc   2640
gggatttggg tcgcggttct tgtttgtgga tcgctgtgat cgtcacttgg tgagtagcgg   2700
gctgctgggc tggccgggc tttcgtggcc gccgggccgc tcggtgggac ggaagcgtgt   2760
ggagagaccg ccaagggctg tagtctgggt ccgcgagcaa ggttgccctg aactgggggt   2820
tgggggagc gcagcaaaat ggcggctgtt cccgagtctt gaatgaaga cgcttgtgag   2880
gcgggctgtg aggtcgttga aacaaggtgg ggggcatggt gggcggcaag aacccaaggt   2940
cttgaggcct tcgctaatgc gggaaagctc ttattcgggt gagatgggct ggggcaccat   3000
ctggggaccc tgacgtgaag tttgtcactg actggagaac tcggtttgtc gtctgttgcg   3060
ggggcggcag ttatggcggt gccgttggc agtgcacccg tacctttggg agcgcgcgcc   3120
ctcgtcgtgt cgtgacgtca cccgttctgt tggcttataa tgcagggtgg ggccacctgc   3180
cggtaggtgt gcggtaggct tttctccgtc gcaggacgca gggttcgggc ctagggtagg   3240
ctctcctgaa tcgacaggcg ccggacctct ggtgagggga gggataagtg aggcgtcagt   3300
ttctttggtc ggttttatgt acctatcttc ttaagtagct gaagctccgg ttttgaacta   3360
tgcgctcggg gttggcgagt gtgtttttgtg aagtttttta ggcacctttt gaatgtaat   3420
catttgggtc aatatgtaat tttcagtgtt agactagtaa attgtccgct aaattctggc   3480
cgtttttggc ttttttgtta gacgcgggat ccgccaccat ggtcttcaca ctcgaagatt   3540
tcgttgggga ctggcgccag acagccggct acaacctaga ccaagtcctt gaacaggag   3600
gtgtgtccag tttgtttcag aatctcgggg tgtccgtaac tccaatccaa aggattgtcc   3660
tgagcgatga aaatgggctg aagatcgaca tccatgtcat catcccatac gaaggtctga   3720
gcggcgacca aatgggccag atcgaaaaaa ttttttaaggt ggtgtaccct gtggatgatc   3780
atcactttaa ggtgatcctg cactatggca cactggtaat cgacggggtt actccaaaca   3840
tgatcgacta tttcggacgg ccatacggaag gcatcgcgct gttcgacggc aaaaagatca   3900
ctgtaacagg gaccctgtgg aacggcaaca aaattatcga cgagcgcctg atcaaccccg   3960
acggctccct gctgttccgc gtaaccatca acggagtgac cggttggaga ctgtgcgaac   4020
gcattctggc gtcgctcgac tcgatggtgt ctaagggcga agagctgatc aaggaaaata   4080
tgcgtatgaa ggtggtcatg gaaggttcgg tcaacggcca ccaattcaaa tgcacaggtg   4140
aaggagaagg caatccgtac atgggaactc aaaccatgag gatcaaagtc atcgaggag   4200
gaccctgcc atttgccttt gacattcttg ccacgtcgtt catgtatggc agccgtactt   4260
ttatcaagta cccgaaaggc attcctgatt tctttaaaca gtccttttcct gagggtttta   4320
cttgggaaag agttacgaga tacgaagatg gtggagtcgt caccgtcatg caggacacca   4380
gccttgagga tggctgtctc gtttaccacg tccaagtcag aggggtaaac tttcctcca   4440
atggtcccgt gatgcagaag aagaccaagg gttgggagcc taatacagag atgatgtatc   4500
cagcagatgg tggtctgagg ggatacactc atatggcact gaaagttgat ggtggtggcc   4560
atctgtcttg ctctttcgta acaacttaca ggtcaaaaaa gaccgtcggg aacatcaaga   4620
tgcccggtat ccatgccgtt gatcaccgcc tggaaaggtt agaggaaagt gacaatgata   4680
tgttcgtagt acaacgcgaa cacgcagttg ccaagttcgc cgggcttggt ggtgggatgg   4740
acgagctgta caagggatct agtggaatgg ttctcatca tcatcatcat catggtatgg   4800
ctagcatgac tggtggacag caaatgggtc gggatctgta cgacgatgac gataaggatc   4860
tcgccaccat ggtcgactca tcacgtcgta agtggaataa gacagtcac gcagtcagg   4920
ctataggtcg gctgagctca ctcgagaacg tctatatcaa ggccgacaag cagaagaacg   4980
gcatcaaggc gaacttcaag atccgccaca acatcgagga cggcggcgtg cagctcgcct   5040
accactacca gcagaacacc cccatcggcg acggccccgt gctgctgccc gacaaccact   5100
acctgagcgt gcagtccaaa ctttcgaaag accccaacga aagcgcgat cacatggtcc   5160
tgctggagtt cgtgaccgcc gccgggatca ctctcggcat ggacgagctg tacaagggcg   5220
gtaccggagg gagcatggtg agcaagggcg aggagctgtt caccggggtg gtgcccatcc   5280
tggtcgagct ggacggcgac gtaaacggcc acaagttcag cgtgtccggc gagggtgagg   5340
gcgatgccac ctacggcaag ctgaccctga agttcatctg caccaccggc aagctgcccg   5400
tgccctggcc cacccctgtg accaccctga cctacggcgt gcagtgcttc agccgctacc   5460
ccgaccacat gaagcagcac gacttcttca agtccgccat gcccgaaggc tacatccagg   5520
agcgcaccat cttcttcaag gacgacggca actacaagac ccgcgccgag gtgaagttcg   5580
agggcgacac cctggtgaac cgcatcgagc tgaagggcac cgacttcaag gaggacggca   5640
acatcctggg gcacaagctg gagtacaacc tgccggacca actgactgaa gagcagatcg   5700
cagaatttaa agaggaattc tcccctatttg acaaggacgg ggatgggaca ataacaacca   5760
aggagctggg gacggtgatg cggtctctgg ggcagaaccc cacagaagca gagctgcagg   5820
acatgatcaa tgaagtagat gccgacggtg acggcacaat cgacttccct gagttcctga   5880
caatgatgc aagaaaaatg aaatacaggg acacggaaga agaaattaga gaagcgttcg   5940
gtgtgtttga taaggatggc aatgctaca tcagtcagc agagcttcgc cacgtgatga   6000
caaaccttga agaagtta acagatgaag aggttgatga aatgatcagg gaagcagaca   6060
tcgatgggga tggtcaggta aactacgaag agtttgtaca aatgatgaca gcgaagtgag   6120
tttaaacggc gcgacatgtt taagggttcc ggttccacta ggtacaattc gatatcaagc   6180
ttatcgataa tcaacctctg gattacaaaa tttgtgaaag attgactggt attcttaact   6240
atgttgctcc ttttacgcta tgtggatacg ctgctttaat gcctttgtat catgctattg   6300
cttcccgtat ggctttcatt ttctcctcct tgtataaatc ctggttgctg tctctttatg   6360
aggagttgtg gcccgttgtc aggcaacgtg gcgtggtgtg cactgtgttt gctgacgcaa   6420
cccccactgg ttggggcatt gccaccacct gtcagctcct ttccgggact ttcgctttcc   6480
ccctccctat tgccacggcg gaactcatcg ccgcctgcct tgccgctgc tggacagggg   6540
ctcggctgtt gggcactgac aattccgtgg tgttgtcggg gaaatcatcg tccttccctt   6600
ggctgctcgc ctgtgttgcc acctggattc tgcgcgggac gtccttctgc tacgtccctt   6660
cggccctcaa tccagcggac cttccttccc gcggcctgct gccggctctg cggcctcttc   6720
cgcgtcttcg ccttcgccct cagacgagtc ggatctccct ttgggccgcc tccccgcatc   6780
gataccgtcg acctcgatcg agaccctgaaa aaacatggag caatcacaag tagcaataca   6840
gcagctacca atgctgattg tgcctggcta gaagcacaag aggaggagga ggtgggtttt   6900
ccagtcacac ctcaggtacc tttaagacca atgacttaca aggcagctgt agatcttagc   6960
cactttttaa agaaaagggg gggactggaa gggctaattc actcccaacg aagacaagat   7020
atccttgatc tgtggatcta ccacacacaa ggctacttcc ctgattggca gaactacaca   7080
ccagggccag gatcagata tccactgacc tttggatggt gctacaagct agtaccagtt   7140
gagcaagaga aggtagaaga agccaatgaa ggagagaaca cccgcttgtt acaccctgtg   7200
agcctgcatg ggatggatga cccggagaga gaagtattag agtggaggtt tgacagccgc   7260
ctagcatttc atcacatggc ccgagagctg catccggact gtactgggtc tctctggtta   7320
```

```
gaccagatct gagcctggga gctctctggc taactaggga acccactgct taagcctcaa  7380
taaagcttgc cttgagtgct tcaagtagtg tgtgcccgtc tgttgtgtga ctctggtaac  7440
tagagatccc tcagacccgt ttagtcagtg tggaaaatct ctagcagcat gtgagcaaaa  7500
ggccagcaaa aggccaggaa ccgtaaaaag gccgcgttgc tggcgttttt ccataggctc  7560
cgcccccctg acgagcatca caaaaatcga cgctcaagtc agaggtggcg aaacccgaca  7620
ggactataaa gataccaggc gtttccccct ggaagctccc tcgtgcgctc tcctgttccg  7680
accctgccgc ttaccggata cctgtccgcc tttctccctt cgggaagcgt ggcgctttct  7740
catagctcac gctgtaggta tctcagttcg gtgtaggtcg ttcgctccaa gctgggctgt  7800
gtgcacgaac cccccgttca gcccgaccgc tgcgccttat ccggtaacta tcgtcttgag  7860
tccaacccgg taagacacga cttatcgcca ctggcagcag ccactggtaa caggattagc  7920
agagcgaggt atgtaggcgg tgctacagag ttcttgaagt ggtggcctaa ctacggctac  7980
actagaagaa cagtatttgg tatctgcgct ctgctgaagc cagttacctt cggaaaaaga  8040
gttggtagct cttgatccgg caaacaaacc accgctggta gcggtggttt ttttgtttgc  8100
aagcagcaga ttacgcgcag aaaaaaagga tctcaagaag atcctttgat cttttctacg  8160
gggtctgacg ctcagtggaa cgaaaactca cgttaaggga ttttggtcat gagattatca  8220
aaaaggatct tcacctagat ccttttaaat taaaatgaa gttttaaatc aatctaaagt  8280
atatatgagt aaacttggtc tgacagttac caatgcttaa tcagtgaggc acctatctca  8340
gcgatctgtc tatttcgttc atccatagtt gcctgactcc ccgtcgtgta gataactacg  8400
atacgggagg gcttaccatc tggccccagt gctgcaatga taccgcgaga cccacgctca  8460
ccggctccag atttatcagc aataaaccag ccagccggaa gggccgagcg cagaagtggt  8520
cctgcaactt tatccgcctc catccagtct attaattgtt gccgggaagc tagagtaagt  8580
agttcgccag ttaatagttt gcgcaacgtt gttgccattg ctacaggcat cgtggtgtca  8640
cgctcgtcgt ttggtatggc ttcattcagc tccggttccc aacgatcaag gcgagttaca  8700
tgatccccca tgttgtgcaa aaaagcggtt agctccttcg gtcctccgat cgttgtcaga  8760
agtaagttgg ccgcagtgtt atcactcatg gttatggcag cactgcataa ttctcttact  8820
gtcatgccat ccgtaagatg cttttctgtg actggtgagt actcaaccaa gtcattctga  8880
gaatagtgta tgcggcgacc gagttgctct tgcccggcgt caatacggga taataccgcg  8940
ccacatagca gaactttaaa agtgctcatc attggaaaac gttcttcggg gcgaaaactc  9000
tcaaggatct taccgctgtt gagatccagt tcgatgtaac ccactcgtgc acccaactga  9060
tcttcagcat cttttacttt caccagcgtt tctgggtgag caaaaacagg aaggcaaaat  9120
gccgcaaaaa agggaataag ggcgacacgg aaatgttgaa tactcatact cttcctttt  9180
caatattatt gaagcattta tcagggttat tgtctcatga gcggatacat atttgaatgt  9240
atttagaaaa ataacaaat aggggtcccg cgcacatttc cccgaaaagt gccacctgac  9300

SEQ ID NO: 3          moltype = DNA   length = 9361
FEATURE               Location/Qualifiers
source                1..9361
                      mol_type = other DNA
                      organism = synthetic construct
SEQUENCE: 3
gtcgacggat cgggagatct cccgatcccc tatggtgcac tctcagtaca atctgctctg   60
atgccgcata gttaagccag tatctgctcc ctgcttgtgt gttggaggtc gctgagtagt  120
gcgcgagcaa aatttaagct acaacaaggc aaggcttgac cgacaattgc atgaagaatc  180
tgcttagggt taggcgtttt gcgctgcttc gcgatgtacg gccagatat cgcgttgaca  240
ttgattattg actagttatt aatagtaatc aattacgggg tcattagttc atagcccata  300
tatggagttc cgcgttacat aacttacggt aaatggcccg cctggctgac cgcccaacga  360
cccccgccca ttgacgtcaa taatgacgta tgttcccata gtaacgccaa tagggacttt  420
ccattgacgt caatgggtgg agtatttacg gtaaactgcc cacttggcag tacatcaagt  480
gtatcatatg ccaagtacgc cccctattga cgtcaatgac ggtaaatggc ccgcctggca  540
ttatgcccag tacatgacct tatgggactt tcctacttgg cagtacatct acgtattagt  600
catcgctatt accatggtga tgcggttttg gcagtacatc aatgggcgtg gatagcggtt  660
tgactcacgg ggatttccaa gtctccaccc cattgacgtc aatgggagtt tgttttggca  720
ccaaaatcaa cgggactttc caaaatgtcg taacaactcc gccccattga cgcaaatggg  780
cggtaggcgt gtacggtggg aggtctatat aagcagcgcg ttttgcctgt actgggtctc  840
tctggttaga ccagatctga gcctgggagc tctctggcta actagggaac ccactgctta  900
agcctcaata agcttgcctt gagtgcttc aagtagtgtg tgcccgtctg ttgtgtgact  960
ctggtaacta gagatccctc agacccttt agtcagtgtg gaaatctct agcagtggcg 1020
cccgaacagg gacttgaaag cgaaaggaa accagaggag ctctctcgac gcaggactcg 1080
gcttgctgaa gcgcgcacgg caagaggcga ggggcggcga ctggtgagta cgccaaaaat 1140
tttgactagc ggaggctaga aggagagaga tgggtgcgag acgtcagta ttaagcgggg 1200
gagaattaga tcgcgatggg aaaaaattcg gttaaggcca gggggaaaga aaaaatataa 1260
attaaaacat atagtatggg caagcaggga gctagaacga ttcgcagtta atcctggcct 1320
gttagaaaca tcagaaggct gtagacaaat actgggacag ctacaaccat cccttcagac 1380
aggatcagaa gaacttagat cattatataa tacagtagca acctctattt gtgtgcatca 1440
aaggatagag ataaaagaca ccaaggaagc tttagacaag atagaggaag agcaaaacaa 1500
aagtaagacc accgcacagc aagcggccgg ccgctgatct tcagacctgg aggaggagat 1560
atgagggaca attggagaag tgaattata aaatataaag tagtaaaaat tgaaccatta 1620
ggagtagcac ccaccaaggc aaagaagaaga gtggtgcaga gagaaaaaag agcagtggga 1680
ataggagctt tgttccttgg gttcttggga gcagcaggaa gcactatggg cgcagcgtca 1740
atgacgctga cggtacaggc cagacaatta ttgtctggta tagtgcagca gcagaacaat 1800
ttgctgaggg ctattgaggc gcaacagcat ctgttgcaac tcacagtctg ggcatcaag 1860
cagctccagg caagaatcct ggctgtgaaa agatacctaa aggatcaaca gctcctgggg 1920
atttggggtt gctctggaaa actcatttgc accactgctg tgccttggaa tgctagttgg 1980
agtaataaat tctctggaaca gatttgaat cacacgagtt ggacagagaa 2040
attaacaatt acacaagctt aatacactcc ttaattgaag aatcgcaaaa ccagcaagaa 2100
aagaatgaac aagaattatt ggaattagat aaatgggcaa gtttgtggaa ttggtttaac 2160
ataacaaatt ggctgtggta tataaaatta ttcataatga gtaggaggc ttggtaggt 2220
ttaagaatag ttttgctgt actttctata gtgaatagag ttaggcaggg atattcacca 2280
ttatcgtttc agacccacct cccaacccg agggacccg acaggcccga aggaatagaa 2340
```

-continued

```
gaagaaggtg gagagagaga cagagacaga tccattcgat tagtgaacgg atcggcactg   2400
cgtgcgccaa ttctgcagac aaatggcagt attcatccac aattttaaaa gaaaagggggg  2460
gattgggggg tacagtgcag gggaaagaat agtagacata atagcaacag acatacaaac   2520
taaagaatta caaaaacaaa ttacaaaaat tcaaatttt cgggtttatt acagggacag    2580
cagagatcca gtttggttag taccgggccc gctctagatc gcatgcggct ccggtgcccg   2640
tcagtgggca gagcgcacat cgcccacagt ccccgagaag ttgtgggag ggtcggccaa    2700
ttgaaccggt gcctagagaa ggtggcgcgg ggtaaactgg gaaagtgatg tcgtgtactg   2760
gctccgcctt tttcccgagg gtgggggaga accgtatata agtgcagtag tcgccgtgaa   2820
cgttctttt cgcaacgggt ttgccgccag aacacaggta agtgccgtgt gtggttcccg    2880
cgggcctggc ctctttacgg gttatgccc ttgcgtgcct tgaattactt ccacctggct    2940
gcagtacgtg attcttgatc ccgagcttcg ggttggaagt gggtgggaga gttcgaggcc   3000
ttgcgcttaa ggagccccctt cgcctcgtgc ttgagttgag gcctggcctg ggcgctgggg  3060
ccgccgcgtg cgaatctggt ggcaccttcg cgcctgtctc gctgctttcg ataagtctct   3120
agccattta aattttgat gacctgctgc gacgcttttt ttctggcaag atagtctct     3180
aaatgcgggc caagatctgc acactggtat ttccgttttt ggggccgcgg gcggcgacgg   3240
ggcccgtgcg tccagcgca catgttcggc gaggcgggc ctgcgagcgc ggccaccgag     3300
aatcggacgg gggtagtctc aagctggccg gcctgctctg gtgcctggcc tcgcgccgcc   3360
gtgtatcgcc ccgccctggg cggcaaggct ggccggtcg gcaccagttg cgtgagcgga    3420
aagatggccg cttccggcc ctgctgcagg gagctcaaaa tggaggacgg ggcgctcggg    3480
agagcgggcg ggtgagtcac ccacacaaag gaaaagggcc tttccgtcct cagccgtcgc   3540
ttcatgtgac tccacggagt accgggcgcc gtccaggcac ctcgattagt tctcgagctt   3600
ttggagtacg tcgtctttag gttgggggga ggggttttat gcgatggagt ttccccacac   3660
tgagtgggtg gagactgaag ttaggccagc ttggcacttg atgtaattct ccttggaatt   3720
tgccctttt gagtttggat cttggttcat tctcaagcct cagacagtgg ttcaaagttt    3780
ttttcttcca tttcaggtgt cgtgaggaat cctctaggtc gacctggatc cggtaccgag   3840
gagatctgcc gccgcgatcg ccggcgcgcc agatctcaag cttaactagc tagcggaccg   3900
acgcgtacgc ggccgctcga cgattataag gatgacgacg ataaattcgt cgagcatcat   3960
caccatcacc attgatgagg tttatccgat ccaccggaat gcattctaga catgtccaat   4020
atgaccgcca tgttgacatt gattattgac tagttattaa tagtaatcaa ttacggggtc   4080
attagttcat agcccatata tggagttccg cgttacataa cttacggtaa atggcccgcc   4140
tggctgaccg cccaacgacc cccgcccatt gacgtcaata atgacgtatg ttcccatagt   4200
aacgccaata gggactttcc attgacgtca atgggtggag tatttacggt aaactgccca   4260
cttggcagta catcaagtgt atcatatgcc aagtccgccc cctattgacg tcaatgacgg   4320
taaatggccc gcctggcatt atgcccagta catgaccttg cgggactttc ctacttggca   4380
gtacatctac gtattagtca tcgctattac catggtgatg cggttttggc agtacaccaa   4440
tgggcgtgga tagcggtttg actcacgggg atttccaagt ctccacccca ttgacgtcaa   4500
tgggagtttg ttttggcacc aaaatcaacg ggactttcca aaatgtcgta ataaccccgc   4560
cccgttgacg caatgggcgg tagcgtgtac ggtgggaggt ctatataagc agagctcgtt   4620
tagtgaaccg tcagaatttt gtaatacgac tcactatagg gcgccggga attcgccacc   4680
atggagagcg acgagagcgg cctgcccgcc atggagatcg agtccgcat caccggcacc   4740
ctgaacggcg tggagttcga gctggtgggc ggcggagagg gcaccccccaa gcagggccgc   4800
atgaccaaca agatgaagag caccaaaggc gccctgacct tcagccccta cctgctgagc   4860
cacgtgatgg gctacggctt ctaccacttc ggcacctacc ccagcggcta cgagaacccc   4920
ttcctgcacg ccatcaacaa cggcggctac accaacaccc gcatcgagaa gtacgaggac   4980
ggcggcgtgc tgcacgtgag cttcagctac cgctacgagg ccggccgcgt gatcggcgac   5040
ttcaaggtgg tgggcaccgg cttccccgag gacagcgtga tcttcaccga caagatcatc   5100
cgcagcaacg ccaccgtgga gcacctgcac cccatgggcg ataacgtgct ggtgggcagc   5160
ttcgcccgca ccttcagcct gcgcgacggc ggctactaca gcttcgtggt ggacagccac   5220
atgcacttca agagcgccat ccaccccagc atcctgcaga acgggggccc catgttcgcc   5280
ttccgccgcg tggaggagct gcacagcaac accgagctgg gcatcgtgga gtaccagcac   5340
gccttcaaga ccccccatcgc cttcgccaga tcccgcgctc agtcgtccaa ttctgccgtg   5400
gacggcaccg ccgaccggg ctccaccgga tctcgcggaa gcggagctac taacttcagc    5460
ctgctgaagc aggctggaga cgtgggaggag aaccctggac ctgtcgacat gaccgagtac   5520
aagcccacgg tgcgcctcgc cacccgcgac gacgtccccc gggcagtacg caccctcgcc   5580
gccgcgttcg ccgactaccc cgccacgcgc cacaccgtcg atccagaccg ccacatcgga   5640
cgggtcaccg agctgcaaga actcttcctc acgcgcgtcg ggctcgacat cggcaaggtg   5700
tgggtcgcgg acgacggcgc cgcggtggc gtctggacca gccgagag cgtcgaagcg     5760
ggggcggtgt tgccgagat cggccgcgcg atggccgagt tgagcggttc ccggctggcc    5820
gcgcagcaac agatggaagg cctcctggcg ccgcaccgg ggaggagcc cgcgtggctc     5880
ctggccaccg tcggcgtctc gcccgaccac cagggcaagg gtctgggcag cgccgtcgtg   5940
ctccccggag tggaggcggc cgagcgcgcc ggggtgcccg ccttcctgga gacctccgcg   6000
ccccgcaacc tccccttcta cgagcggctc ggcttcaccg tcaccgccga cgtcgaggtg   6060
cccgaaggac cgcgcacctg gtgcatgacc cgcaagcccg gtgcctgagt taaacgggc    6120
cggccgcggt ctgtacaagt aggattcgtc gagggaccta ataacttcgt atagcataca   6180
ttatacgaag ttatacatgt ttaagggttc cggttccact aggtacaatt cgatatcaag   6240
cttatcgata atcaacctct ggattacaaa atttgtgaaa gattgactgg tattcttaac   6300
tatgttgctc cttttacgct atgtggatac gctgctttaa tgcctttgta tcatgctatt   6360
gcttcccgta tggctttcat ttttctcctcc ttgtataaat cctggttgct gtctctttat   6420
gaggagttgt ggcccgttgt caggcaacgt ggcgtggtgt gcactgtgtt tgctgacgca   6480
acccccactg gttggggcat tgccaccacc tgtcagctcc tttccgggac tttcgctttc   6540
cccctcccta ttgccacggc ggaactcatc gccgcctgcc ttgcccgctg ctggacaggg   6600
gctcggctgt tgggcactga caattccgtg gtgttgtcgg ggaaatcatc gtcctttcct   6660
tggctgctcg cctgtgttgc cacctggatt ctgcgcggga cgtccttctg ctacgtccct   6720
tcggccctca atccagcgga ccttccttcc cgcggcctgc tgccggctct gcggcctctt   6780
ccgcgtcttc gccttcgccc tcagacgagt cggatctccc tttgggccgc ctccccgcat   6840
cgataccgtc gacctcgatc gagacctaga aaaacatgga gcaatcacaa gtagcaatac   6900
agcagctacc aatgctgatt gtgcctggct agaagcacaa gaggaggagg aggtgggttt   6960
tccagtcaca cctcaggtac cttttaagacc aatgacttac aaggcagctg tagatcttag   7020
ccacttttta aagaaaagg ggggactgga aggggctaatt cactcccaac gaagacaaga   7080
```

```
tatccttgat ctgtggatct accacacaca aggctacttc cctgattggc agaactacac    7140
accagggcca gggatcagat atccactgac ctttggatgg tgctacaagc tagtaccagt    7200
tgagcaagag aaggtagaag aagccaatga aggagagaac accgcttgt tacaccctgt     7260
gagcctgcat gggatggatg acccggagag agaagtatta gagtggaggt ttgacagccg    7320
cctagcattt catccacatg cccgagagct gcatccgaca tgtactgggt ctctctggtt    7380
agaccagatc tgagcctggg agctctctgg ctaactaggg aacccactgc ttaagcctca    7440
ataaagcttg ccttgagtgc ttcaagtagt gtgtgcccgt ctgttgtgtg actctggtaa    7500
ctagagatcc ctcagaccct tttagtcagt gtggaaaatc tctagcagca tgtgagcaaa    7560
aggccagcaa aaggccagga accgtaaaaa ggccgcgttg ctggcgtttt tccataggct    7620
ccgcccccct gacgagcatc acaaaaatcg acgctcaagt cagaggtggc gaaacccgac    7680
aggactataa agataccagg cgtttccccc tggaagctcc ctcgtgcgct ctcctgttcc    7740
gaccctgccg cttaccggat acctgtccgc ctttctccct tcgggaagcg tggcgctttc    7800
tcatagctca cgctgtaggt atctcagttc ggtgtaggtc gttcgctcca agctgggctg    7860
tgtgcacgaa ccccccgttc agcccgaccg ctgcgcctta tccggtaact atcgtcttga    7920
gtccaacccg gtaagacacg acttatcgcc actggcagca gccactggta acaggattag    7980
cagagcgagg tatgtaggcg gtgctacaga gttcttgaag tggtggccta actacggcta    8040
cactagaaga acagtatttg gtatctgcgc tctgctgaag ccagttacct tcggaaaaag    8100
agttggtagc tcttgatccg gcaaacaaac caccgctggt agcggtggtt tttttgtttg    8160
caagcagcag attacgcgca gaaaaaaagg atctcaagaa gatcctttga tcttttctac    8220
ggggtctgac gctcagtgga acgaaaactc acgttaaggg attttggtca tgagattatc    8280
aaaaaggatc ttcacctaga tccttttaaa ttaaaaatga agttttaaat caatctaaag    8340
tatatatgag taaacttggt ctgacagtta ccaatgctta atcagtgagg cacctatctc    8400
agcgatctgt ctatttcgtt catccatagt tgcctgactc cccgtcgtgt agataactac    8460
gatacgggag ggcttaccat ctggccccag tgctgcaatg ataccgcgag acccacgctc    8520
accggctcca gatttatcag caataaacca gccagccgga agggccgagc gcagaagtgg    8580
tcctgcaact ttatccgcct ccatccagtc tattaattgt tgccgggaag ctagagtaag    8640
tagttcgcca gttaatagtt tgcgcaacgt tgttgccatt gctacaggca tcgtggtgtc    8700
acgctcgtcg tttggtatgg cttcattcag ctccggttcc caacgatcaa ggcgagtac    8760
atgatccccc atgttgtgca aaaaagcggt tagctccttc ggtcctccga tcgttgtcag    8820
aagtaagttg gccgcagtgt tatcactcat ggttatgcca cactgcata attctcttac    8880
tgtcatgcca tccgtaagat gcttttctgt gactggtgag tactcaacca agtcattctg    8940
agaatagtgt atgcggcgac cgagttgctc ttgcccggcg tcaatacggg ataataccgc    9000
gccacatagc agaactttaa aagtgctcat cattggaaaa cgttcttcgg ggcgaaaact    9060
ctcaaggatc ttaccgctgt tgagatccag ttcgatgtaa cccactcgtg cacccaactg    9120
atcttcagca tcttttactt tcaccagcgt ttctgggtga gcaaaaacag gaaggcaaaa    9180
tgccgcaaaa aagggaataa gggcgacacg gaaatgttga atactcatac tcttcctttt    9240
tcaatattat tgaagcattt atcagggtta ttgtctcatg agcggataca tatttgaatg    9300
tatttagaaa aataaacaaa taggggtccc gcgcacattt ccccgaaaag tgccacctga    9360
c                                                                   9361

SEQ ID NO: 4           moltype = DNA   length = 39
FEATURE                Location/Qualifiers
source                 1..39
                       mol_type = other DNA
                       organism = synthetic construct
SEQUENCE: 4
actagtggaa tgggttctca tcatcatcat catcatggt                          39

SEQ ID NO: 5           moltype = DNA   length = 31
FEATURE                Location/Qualifiers
source                 1..31
                       mol_type = other DNA
                       organism = synthetic construct
SEQUENCE: 5
gtttaaactc acttcgctgt catcatttgt a                                  31

SEQ ID NO: 6           moltype = DNA   length = 32
FEATURE                Location/Qualifiers
source                 1..32
                       mol_type = other DNA
                       organism = synthetic construct
SEQUENCE: 6
ggatccatgg tcttcacact cgaagatttc gt                                 32

SEQ ID NO: 7           moltype = DNA   length = 35
FEATURE                Location/Qualifiers
source                 1..35
                       mol_type = other DNA
                       organism = synthetic construct
SEQUENCE: 7
tctagatccc ttgtacagct cgtccatccc accac                              35

SEQ ID NO: 8           moltype = AA    length = 4
FEATURE                Location/Qualifiers
source                 1..4
                       mol_type = protein
                       organism = synthetic construct
SEQUENCE: 8
SLDS                                                                4
```

| | | |
|---|---|---|
| SEQ ID NO: 9 | moltype = AA length = 4 | |
| FEATURE | Location/Qualifiers | |
| source | 1..4 | |
| | mol_type = protein | |
| | organism = synthetic construct | |
| SEQUENCE: 9 | | |
| GSSG | | 4 |

What is claimed is:

1. A fusion imaging gene, wherein the fusion imaging gene comprises a bioluminescence imaging gene, a fluorescent protein gene and a calcium imaging gene, and the three genes are linked by linkers;
the bioluminescence imaging gene is selected from a Nanoluc gene;
the fluorescent protein gene is selected from a mRuby2 gene;
the calcium imaging gene is selected from a Gcamp6f gene;
the Nanoluc gene and the mRuby2 gene are linked through Linker 1, as shown in SEQ ID NO.8; the mRuby2 gene and the Gcamp6f gene are linked through Linker 2, as shown in SEQ ID NO.9;
a nucleotide sequence of the fusion imaging gene is shown in SEQ ID NO.1.

2. A method for constructing the fusion imaging gene according to claim 1, at least comprising following steps:
S11, obtaining a Nanoluc gene sequence, removing a tail stop codon, and adding one S amino acid gene sequence and an XhoI restriction site sequence at a tail end of the Nanoluc gene;
S12, obtaining a mRuby2 gene sequence, removing a tail stop codon, and adding a SalI restriction site sequence and one S amino acid at a front end of the mRuby2 gene successively; adding one G amino acid sequence and an XbaI restriction site sequence to a back end of the mRuby2;
S13, obtaining a Gcamp6f gene sequence, adding one G amino acid and a SpeI restriction site at a front end of the Gcamp6f gene, and adding a PmeI restriction site at a tail end of the gene;
S14, using an XhoI restriction site at the tail end of Nanoluc and the SalI restriction site at the front end of mRuby2 for respectively cutting the Nanoluc gene and the XhoI restriction site with an XhoI enzyme and a SalI enzyme, and respectively obtaining an enzyme-digested product of the Nanoluc gene and an enzyme-digested product of the mRuby2 gene after purification;
S15, linking the enzyme-digested product of the Nanoluc gene with the enzyme-digested product of the mRuby2 gene, and amplifying, purifying, linking to a T vector, transforming competent cells, culturing and sequencing to obtain a Nanoluc-S-L-D-S-mRuby2 plasmid;
S16, amplifying the Gcamp6f gene by PCR, treating the Nanoluc-S-L-D-S-mRuby2 plasmid with an XbaI enzyme, treating the Gcamp6f gene with a SpeI enzyme, and purifying the enzyme-digested products; and
S17, linking a Nanoluc-S-L-D-S-mRuby2 gene and the Gcamp6f gene, amplifying, purifying, linking to a T vector, transforming competent cells, culturing and sequencing to obtain a strain containing the fusion imaging gene.

3. The method for constructing the fusion imaging gene according to claim 2, wherein in the S11, the Nanoluc gene sequence is synthesized by the gene.

4. The method for constructing the fusion imaging gene according to claim 2, wherein in the S12, the mRuby2 gene sequence is synthesized by the gene.

5. The method for constructing the fusion imaging gene according to claim 2, wherein in the S13, the Gcamp6f gene sequence is obtained by PCR.

6. The method for constructing the fusion imaging gene according to claim 5, wherein in the S13, primer sequences are shown in SEQ ID NO.4 and SEQ ID NO.5.

7. A lentiviral expression plasmid carrying the fusion imaging gene according to claim 1.

8. The lentiviral expression plasmid of fusion imaging gene according to claim 7, wherein a sequence of the lentiviral expression plasmid carrying fusion imaging gene is shown in SEQ ID NO.2.

9. A preparation method of lentiviral expression plasmid, at least comprising following steps:
S21, modifying the lentiviral expression plasmid; and
S22, inserting the fusion imaging gene according to claim 1 into a modified lentiviral expression plasmid to obtain the lentiviral expression plasmid carrying a fusion gene probe.

10. The preparation method of lentiviral expression plasmid according to claim 9, wherein in the S21, the modifying comprises:
S211, removing an EF-1α promoter in a pLenti-EF1α-FH-CMV-CopGFP&Puro plasmid by double restriction endonuclease digestion with SphI and BamHI to obtain a skeleton plasmid; wherein a nucleotide sequence of the pLenti-EF1α-FH-CMV-CopGFP&Puro plasmid is shown in SEQ ID NO.3;
S212, inserting a human ubiquitin promoter hUbc into the skeleton plasmid through enzyme link to obtain a pLenti-Ubc-FH-CMV-CopGFP&Puro intermediate plasmid; and
S213, removing a sequence from a downstream of Ubc to a Puro gene site in the pLenti-Ubc-FH-CMV-CopGFP&Puro plasmid by PmeI and BamHI double digestion, namely a nucleotide sequence from 3826 to 6112 in the nucleotide sequence shown in the SEQ ID NO.3.

11. The preparation method of lentiviral expression plasmid according to claim 9, wherein in the S22, the fusion imaging gene are inserted into the modified intermediate plasmid by using same restriction sites at both ends of the fusion imaging gene to obtain a pLenti-Ubc-Nanoluc-mRuby2-Gcamp6f plasmid, and the lentiviral expression plasmid is obtained through transformation, sequencing, and so on, and a nucleotide sequence of the lentiviral expression plasmid is shown in SEQ ID NO.2.

12. A lentivirus carrying the fusion imaging gene according to claim 1.

13. A preparation method of the lentivirus according to claim 12, at least comprising following steps:
 co-transfecting 293T cells by the plasmid shown in the SEQ ID NO.2 and lentivirus packaging plasmids PAX2 and pMD2G to obtain lentivirus particles carrying the fusion imaging gene.

14. The preparation method of the lentivirus according to claim 13, wherein a mass ratio of the plasmid shown in the SEQ ID NO.2, the plasmid PAX2 and the plasmid pMD2G3 is 3-4:1.5-2.5:0.5-1.5.

15. The preparation method of the lentivirus according to claim 13, wherein the mass ratio of the plasmid shown in the SEQ ID NO.2, the plasmid PAX2 and the plasmid pMD2G3 is 3:2:1.

16. A cell marked by the fusion imaging gene according to claim 1.

17. A cell marked by the fusion imaging gene according to claim 1, wherein the cell is a human H1 embryonic stem cell or a human pluripotent stem cell.

\* \* \* \* \*